(12) United States Patent
Deangeli et al.

(10) Patent No.: US 12,253,512 B1
(45) Date of Patent: Mar. 18, 2025

(54) APPARATUS AND METHODS FOR IDENTIFICATION OF MICROBIAL PRESENCE

(71) Applicant: Oxbridge Clinical Inc., Boston, MA (US)

(72) Inventors: Giulio Deangeli, Boston, MA (US); Cristiano Peron, Boston, MA (US)

(73) Assignee: Oxbridge Clinical Inc., Boston, MA (US)

( * ) Notice: Subject to any disclaimer, the term of this patent is extended or adjusted under 35 U.S.C. 154(b) by 0 days.

(21) Appl. No.: 18/663,425

(22) Filed: May 14, 2024

(51) Int. Cl.
*G01N 33/487* (2006.01)

(52) U.S. Cl.
CPC .............. *G01N 33/48721* (2013.01)

(58) Field of Classification Search
CPC ................................. G01N 33/48721
See application file for complete search history.

(56) References Cited

U.S. PATENT DOCUMENTS

2021/0148885 A1   5/2021   Ching-Shun

FOREIGN PATENT DOCUMENTS

WO   2020112604 A2   6/2020
WO   2021093220 A1   5/2021

OTHER PUBLICATIONS

Akhide Arima et al; Selective detections of single-viruses using solid-state nanopores; "Scientific Reports vol. 8, Article No. 16305 (2018), Published: Nov. 2, 2018".

Shiva Akhtarian et al; Nanopore sensors for viral particle quantification: current progress and future prospects; "Bioengineered. 2021; 12(2): 9189-9215.Published online Nov. 22, 2021".

Chenyu Wen et al Return to Issueprevreviewnext A Guide to Signal Processing Algorithms for Nanopore Sensors; ACS Sens. 2021, 6, 10, 3536-3555, Publication Date:Oct. 4, 2021.

*Primary Examiner* — Narayan K Bhat
(74) *Attorney, Agent, or Firm* — Caldwell Intellectual Property Law

(57) ABSTRACT

Apparatus and methods for identification of microbial presence are described, wherein the apparatus includes at least a nanopore, at least a nanopore reader, and a control unit, wherein each of the at least a nanopore reader comprises a plurality of flow cells, at least one of which is configured to accept a sample, and at least a detector connected to the plurality of flow cells and configured to detect a signal as a function of at least a translocated microbe from the sample, wherein the control unit is communicatively connected to the at least a detector and configured to receive the detected signal, correlate its intensity with at least an attribute of the detected signal, and determine at least an identity of the at least a translocated microbe as a function of the correlation.

30 Claims, 12 Drawing Sheets

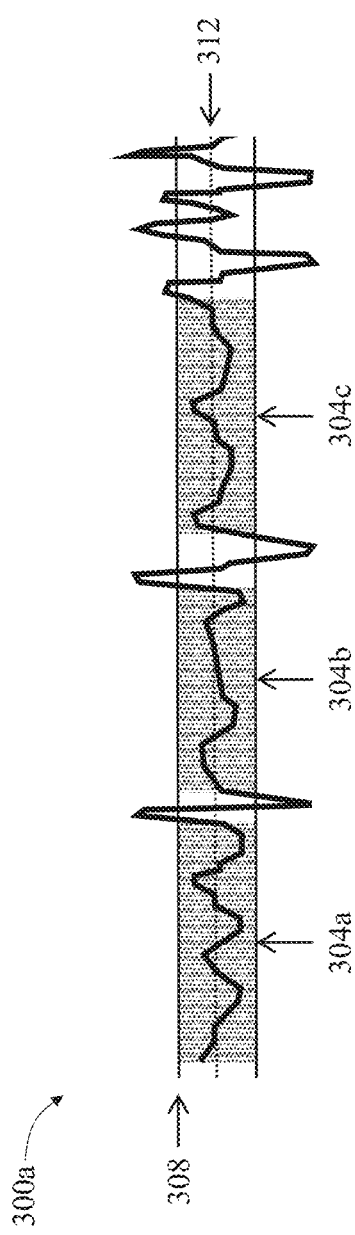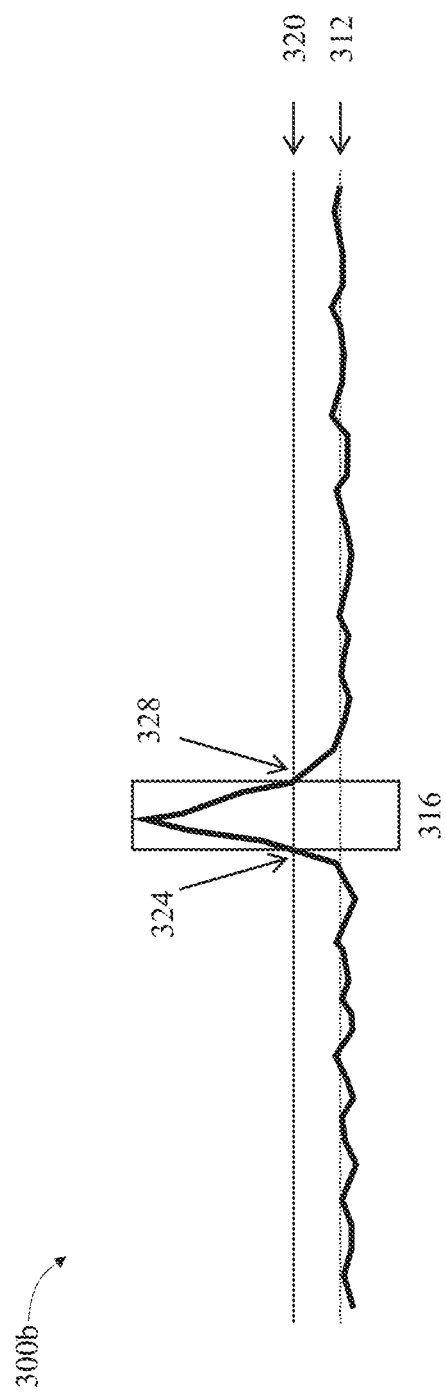

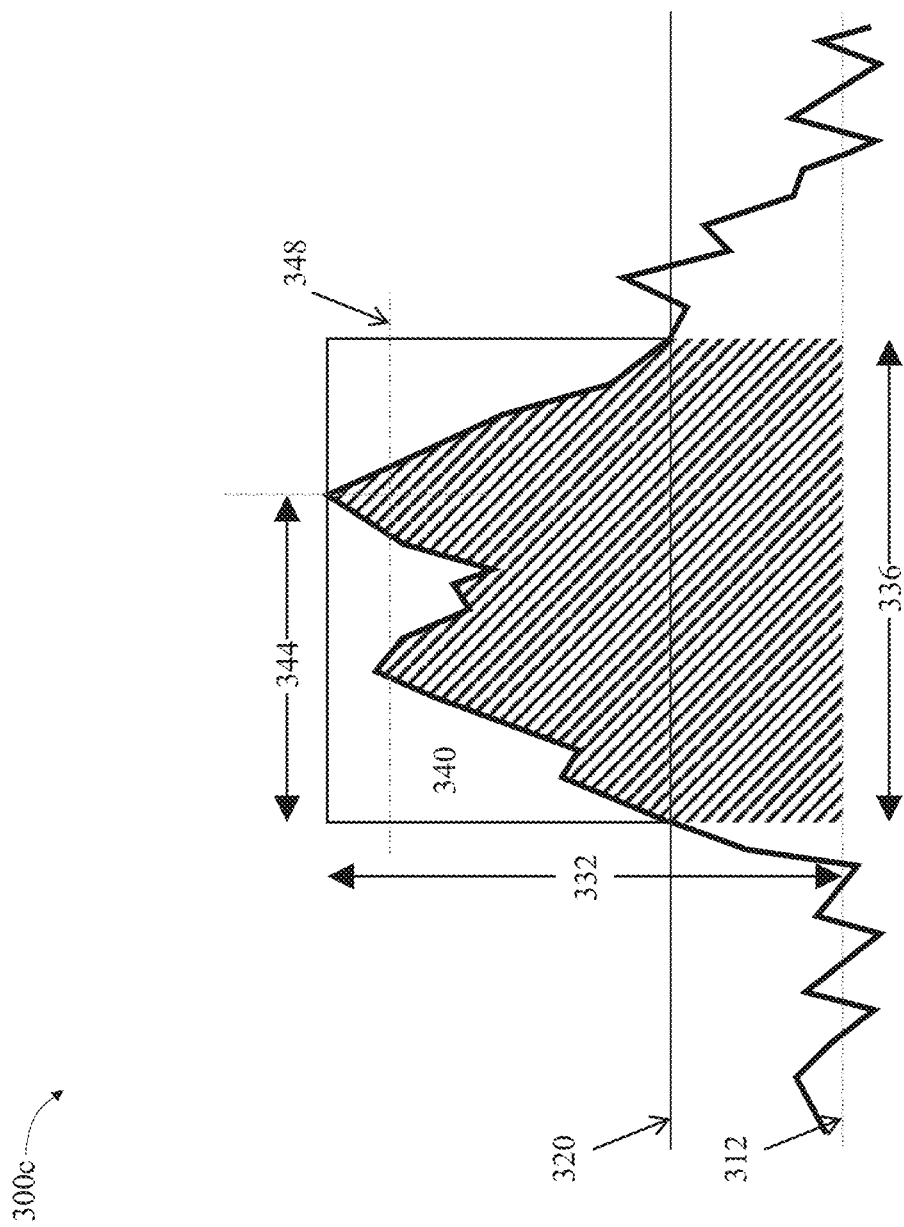

APPARATUS AND METHODS FOR IDENTIFICATION OF MICROBIAL PRESENCE

FIELD OF THE INVENTION

The present invention generally relates to the field of identification of microbes. In particular, the present invention is directed to an apparatus that detects and identifies a presence of microbes using one or more nanopores.

BACKGROUND

Identification of microbial contamination, in the form of viral, bacterial, or fungal microorganisms, poses a constant threat to public health in several fields, including human and veterinary infectious diseases, food poisoning, and sewage waters. One application related thereto is constituted by the identification of pathogens in a respiratory sample, from patients suffering from respiratory tract infections (RTIs). Most current tools for germ-specific microbial detection rely on nucleic acid-based or antibody-based technologies, which may be costly, hard to deploy at the point of care, and inherently germ-specific, that is, the test must be performed at least once for each pathogen to be tested. Alternatively, another tool is represented by microbial cultures, which however suffer from a significant delay in result availability, as they require the pathogens to undergo repeated reproduction cycles to become identifiable.

SUMMARY OF THE DISCLOSURE

In one aspect, an apparatus for identification of microbial presence is described. The apparatus includes a plurality of nanopores, at least a nanopore reader, and a control unit. Each nanopore reader includes a plurality of flow cells, at least one of which is configured to accept a sample, and at least a detector connected to the flow cells and configured to detect a signal as a function of at least a translocated microbe from the sample. The control unit is communicatively connected to the detector and configured to receive the detected signal, identify at least an event from the detected signal, correlate the intensity of the identified at least an event with at least an attribute of the identified at least an event, and determine at least an identity of the translocated microbe as a function of the correlation.

In another aspect, another apparatus for identification of microbial presence is described. The apparatus includes a nanopore, a nanopore reader, and a control unit. The nanopore reader includes a plurality of flow cells, at least one of which is configured to accept a sample, and at least a detector connected to the flow cells and configured to detect a signal as a function of at least a translocated microbe from the sample. The control unit is communicatively connected to the detector and configured to receive the detected signal, identify at least an event from the detected signal, correlate the intensity of the identified at least an event with at least an attribute of the identified at least an event, and determine at least an identity of the translocated microbe as a function of the correlation.

In another aspect, a method for identification of microbial presence is described. The method includes accepting, by a first flow cell, a sample including at least a microbe, detecting, by at least a detector, a signal as a function of the at least a microbe, wherein the at least a microbe is translocated from the first flow cell to a second flow cell through at least a nanopore, receiving, by a control unit, the detected signal from the at least a detector, identifying, by the control unit, at least an event from the detected signal, correlating, by the control unit, the intensity of the identified at least an event with at least an attribute of the identified at least an event, and determining, by the control unit, at least an identity of the at least a translocated microbe as a function of the correlation.

These and other aspects and features of nonlimiting embodiments of the present invention will become apparent to those of ordinary skill in the art upon reviewing the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 3A is an exemplary embodiment of an extended signal containing a plurality of flat intervals.

FIG. 3B is an exemplary embodiment of an identified event between two flanking flat intervals.

FIG. 3C is an exemplary embodiment of several attributes that describe an identified event.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for identification of microbial presence using solid-state nanopores. The apparatus includes at least a nanopore, at least a nanopore reader, and a control unit, wherein the nanopore reader includes a plurality of flow cells and at least a detector. Translocation of a microbe from one flow cell to another, through a nanopore, may result in a detection of a signal and/or an identification of an event. Exemplary embodiments of the apparatus include both single-nanopore and multiple-nanopore configurations. In one or more embodiments, multiple nanopores may be arranged in a line, in a two-dimensional (2D) matrix, or in a three-dimensional (3D) matrix. In one or more embodiments, multiple nanopores may be in various sizes, constructed in various geometries, different surface material, excavated within/coated by various types of materials, and/or subject to various voltage differences, to maximize their selectivity in detecting translocated microbes of various sizes, shapes, and/or surface charges. In one or more embodiments, detection of a translocated microbe may result in a resistive pulse, wherein correlations between the height of the resistive pulse and several other attributes may reveal signatures that are unique to the identity of microbe.

Aspects of the present disclosure may be used for diagnostic tools that are affordable, efficient, and capable of being deployed directly on the field, or at point of care for clinical applications.

Figure 1:
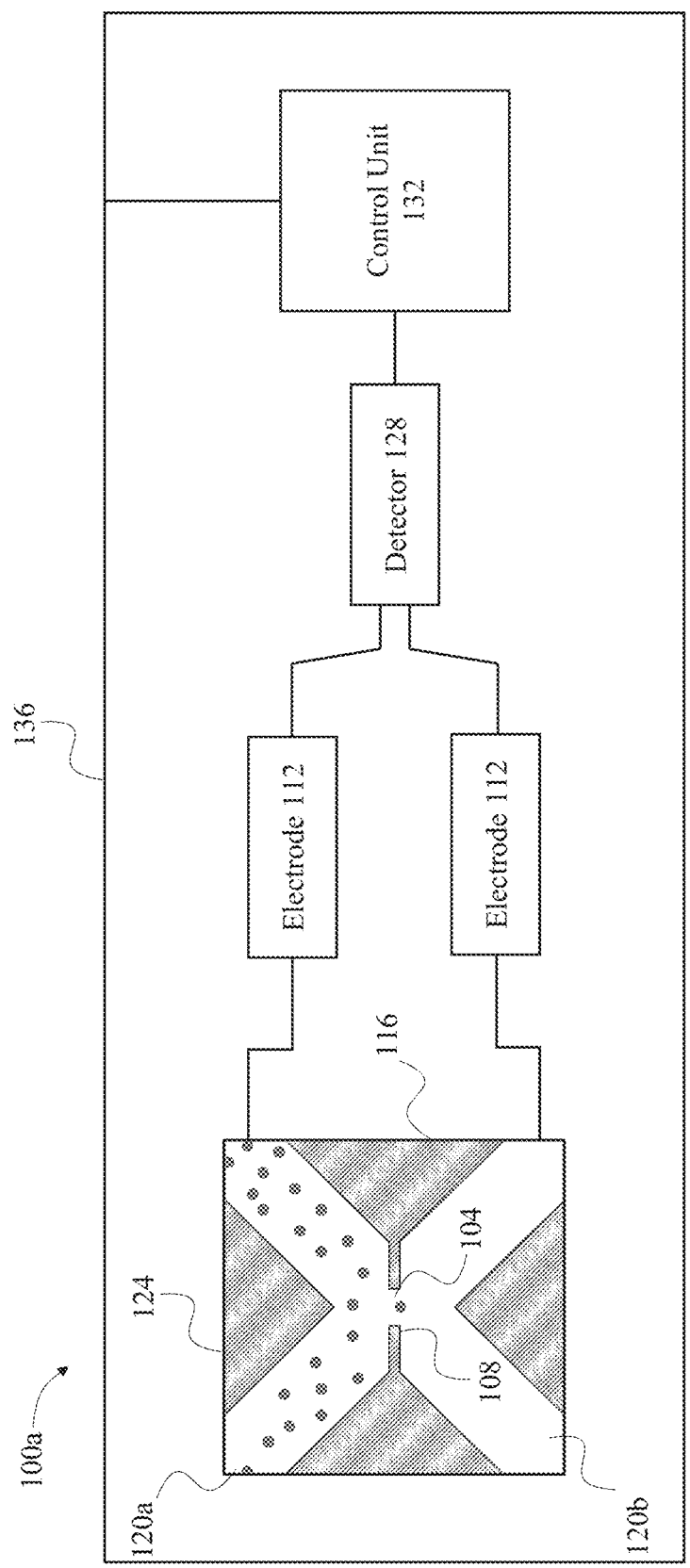
FIG. 1 is a schematic illustration of an exemplary embodiment of an apparatus for identification of microbial presence.

Referring now to FIG. 1, an exemplary embodiment 100a of apparatus 100 for identification of microbial presence is illustrated. Apparatus 100 comprises at least a nanopore 104. For the purposes of this disclosure, a "nanopore" is a hollow cavity or channel with two orifices/open ends and a lateral dimension on a nanometer-to-micrometer scale; in other words, for the purposes of this disclosure, the word "nanopore" is intended to represent both nanopores and micropores. In one or more embodiments, a nanopore may have a lateral dimension between 100 nanometers and 20 micrometers. For the purposes of this disclosure, a "longitudinal" direction of a nanopore is the direction that extending from one opening to the other, whereas a "lateral" direction is the direction that is transverse (i.e., perpendicular to) the longitudinal direction; a "lateral dimension" of a nanopore is the size of the nanopore along its lateral direction. Nanopore 104 may be constructed within a thin-layer matrix 108 of any durable solid-state matrix or material considered suitable (e.g., both mechanically robust during processing and electrically non-conductive) by a person of ordinary skill in the art upon reviewing the entirety of this disclosure. In one or more embodiments, nanopore 104 may be excavated in a membrane of organic materials, such as without limitation polyimides (PIs). In one or more embodiments, nanopore 104 may be excavated in a glass wafer, such as without limitation a fused-silica wafer. In one or more embodiments, nanopore 104 may be excavated in a $SiN_x$ wafer. For the purposes of this disclosure, $SiN_x$ or silicon nitride is a type of ceramic material containing one or more compounds formed by silicon (Si) and nitrogen (N); the ratio between Si and N in $SiN_x$ is typically 3:4 but may vary from case to case. In one or more embodiments, nanopore 104 may be coated/lined with a secondary material, such as aluminum oxide ($AlO_x$) or silicon oxide ($SiO_x$), either across an extended surface area of thin-layer matrix 108 or only locally at the pore, to fine-tune its chemical properties such as surface charges. In another non-limiting embodiment, a pore surface of at least a first nanopore of the plurality of nanopores is made of a first material, and a pore surface of at least a second nanopore of the plurality of nanopores is made of a second material, wherein the first material is different from the second material. In some cases, the elemental ratio within coating material or materials may be fine-tuned to achieve certain enrichment or deficiency of one or more elements, and such variations may create new properties not present in their stoichiometric analogues. As a nonlimiting example, in aluminum oxide, the ratio between $Al^{3+}$ and $O^{2-}$ may be synthetically tuned to deviate from 1:3. In one or more embodiments, nanopore 104 may be excavated in glass. In one or more embodiments, two potentials/voltages may be applied, for example and without limitation, through two electrodes 112, at the two open ends of nanopore 104, resulting in a voltage difference across longitudinal axis of nanopore 104. In one or more embodiments, apparatus 100 may include only one nanopore 104. In one or more embodiments, apparatus 100 may include a plurality of nanopores 104. In some cases, plurality of nanopores 104 may be arranged in a line. In some cases, plurality of nanopores 104 may be arranged in a two-dimensional (2D) array or matrix. In some cases, plurality of nanopores 104 may be arranged in a three-dimensional (3D) array or matrix. In some cases, plurality of nanopores 104 may be dispersed over a plurality of locations, wherein each location of the plurality of locations contains either a single nanopore 104 or a cluster of multiple nanopores 104.

With continued reference to FIG. 1, apparatus 100 comprises at least a nanopore reader 116. Each nanopore reader 116 of the at least a nanopore reader 116 comprises a plurality of flow cells 120, wherein at least a flow cell 120 within the plurality of flow cells 120 is configured to accept a sample. Flow cell 120 may be constructed from any suitable material recognized by a person of ordinary skill in the art upon reviewing the entirety of this disclosure; suitable materials may include, for example and without limitation, quartz, glass, polyethylene, polypropylene, poly(methyl methacrylate) (PMMA), polyimides (PIs), polydimethylsiloxane (PDMS), or the like. Alternatively and/or additionally, flow cell 120 may be constructed in any shape or design that's deemed suitable for apparatus 100 by a person of ordinary skill in the art upon reviewing the entirety of this disclosure. In some cases, thin-layer matrix 108 containing nanopore 104 may be fused with one more flow cells 120 in one piece, or otherwise in contact or integrated with one or more flow cells 120. Sample may come from any source where at least a microbe of interest may be found. As a nonlimiting example, samples may be collected from clinical samples such as respiratory swab, bronchoalveolar lavage, blood, saliva, and urine. As another nonlimiting example, samples may be collected from veterinary samples, food, sewage, or the like. In one or more embodiments, a first flow cell 120a within plurality of flow cells 120 is configured to accept a sample, a second flow cell 120b within plurality of flow cells 120 is configured to accept a reference (i.e., a solution of known identity, concentration, and physical/chemical properties to which sample may be compared to result in one or more measurements), wherein the first flow cell 120a intersects the second flow cell 120b at a junction 124, and at least a nanopore 104, as described above, is located at the junction 124 and connecting between the first flow cell 120a and the second flow cell 120b. Each of first flow cell 120a and second flow cell 120b may contain at least an opening along its pathlength, wherein the at least an opening of flow cell 120a may face the at least an opening of flow cell 120b and be separated by nanopore 104. As a nonlimiting example, sample may be prepared in phosphate-buffered saline (PBS) solution, whereas reference may be a blank phosphate-buffered saline (PBS) solution. For the purposes of this disclosure, a "junction" is a point of contact that joins first flow cell 120a, second flow cell 120b, and nanopore 104 together, such that one or more species (ions, molecules, microbes, or the like) may pass through the nanopore 104, with various extents of selectivity, from one flow cell 120 to the other, in either direction.

With continued reference to FIG. 1, apparatus 100 comprises at least a detector 128 connected to plurality of flow cells 120, wherein the at least a detector 128 is configured to detect a signal as a function of at least a translocated microbe from sample. For the purposes of this disclosure, a "signal" is any intelligible representation of data, for example from one device to another. A signal may include an optical signal, a hydraulic signal, a pneumatic signal, a mechanical signal, an electric signal, a digital signal, an analog signal, and the like. In some cases, a signal may be used to communicate with a computing device, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like. "Signal", "trace", and "signal trace" may be used interchangeably throughout this disclosure. In one or more embodiments, signal may be an electrical signal, which may include and/or be generated by a change to any electrical parameter that results from an event or object to be detected. Exemplary types of electrical signal include, without limitation, electrical current, voltage difference (e.g., bias or zeta potential), impedance, capacitance, inductance, or the like. In one or more embodiments, signal may be an optical signal within at least a characteristic wavelength, frequency, and amplitude within the electromagnetic spectrum, such as absorbance, light scattering, fluorescence, phosphorescence, rotational and/or vibrational signatures, or any similar applicable spectroscopic features recognized by a person of ordinary skill in the art upon reviewing the entirety of this disclosure. A signal may contain one or more events to be identified. For the purposes of this disclosure, an "event" is an occurrence of change within a spatial and/or temporal trace of data (i.e., a signal) that deviates from a stable baseline value beyond a certain detection threshold and potentially contains useful information related to one or more functions of apparatus 100, as described below in this disclosure. In one or more embodiments, signal may rise and decay as a function of time and/or space to result in at least an event with a shape of a peak or pulse, with one or more attributes embedded therein, as described below.

With continued reference to FIG. 1, for the purposes of this disclosure, a detector 128 is a device configured to capture at least a signal and/or one or more events contained therein, as described below. In one or more embodiments, detector 128 may be an electrical detector that detects one or more changes in electrical signal due to translocation of microbe (e.g., as microbe enters or leaves nanopore 104). Detector 128 may include an ammeter, a voltmeter, and/or one or more variations thereof. As a nonlimiting example, signal may be detected by detector 128 as a resistive pulse (i.e., a spike of increased electrical resistance) due to a displacement/exclusion of conductive species from nanopore 104 as one or more microbes are translocated therethrough. In one or more embodiments, detector 128 may be a photodetector that detects one or more changes in optical signal due to translocation of microbe (e.g., as microbe enters or leaves nanopore 104). For the purposes of this disclosure, a "photodetector" is a device or component that, upon receiving at least a photon, generates a measurable change in at least an electrical parameter within a circuit incorporating the photodetector; as a result, other components of the circuit may amplify, detect, record, or otherwise use the signal for purposes that include without limitation analysis of the detected at least a photon, which may be combined with analyses of photons detected by other photodetectors, imaging based on detected photons, and other similar purposes. Photodetector may include, without limitation, avalanche photodiodes (APDs), single photon avalanche diodes (SPADs), silicon photomultipliers (SiPMs), photo-multiplier tubes (PMTs), micro-channel plates (MCPs), micro-channel plate photomultiplier tubes (MCP-PMTs), indium gallium arsenide semiconductors (InGaAs), photodiodes, and/or photosensitive or photon-detecting circuit elements, semiconductors and/or transducers. For the purposes of this disclosure, avalanche photo diodes (APDs) are diodes (e.g. without limitation p-n, p-i-n, and others) reverse-biased such that a single photo-generated carrier can trigger a short, temporary "avalanche" of photocurrent on the order of milliamps or more caused by electrons being accelerated through a high field region of the diode and impact-ionizing covalent bonds in the bulk material, these in turn triggering greater impact ionization of electron-hole pairs. APDs provide a built-in stage of gain through avalanche multiplication. When the reverse bias is less than the breakdown voltage, the gain of the APD is approximately linear. For silicon APDs, this gain is on the order of 10-100. Material of APD may contribute to gains. Germanium APDs may detect infrared out to a wavelength of 1.7 micrometers. InGaAs may detect infrared out to a wavelength of 1.6 micrometers. Mercury Cadmium Telluride (HgCdTe) may detect infrared out to a wavelength of 14 micrometers. An APD reverse-biased significantly above the breakdown voltage is referred to as a single photon avalanche diode, or SPAD. In this case, the n-p electric field is sufficiently high to sustain an avalanche of current with a single photon, hence referred to as "Geiger mode". This avalanche current rises rapidly (on a sub-nanosecond timescale), such that detection of the avalanche current can be used to approximate the arrival time of the incident photon. The SPAD may be pulled below breakdown voltage once triggered in order to reset or quench the avalanche current before another photon may be detected, as while the avalanche current is active, carriers from additional photons may have a negligible effect on the current in the diode.

With continued reference to FIG. 1, a plurality of photodetectors may be in close proximity to each other. For instance, each photodetector may be placed directly next to neighboring photodetectors of plurality of photodetectors, for instance in a two-dimensional grid, a grid on a curved surface or manifold, or the like. Placement in close proximity may eliminate or reduce to a negligible level spatially dependent variation in received signals, permitting a control circuit, as described below, to infer other causes for signal variation between detectors. As a nonlimiting example, an array of photodetectors may be comprised of photodetectors occupying a length or breadth of less than 25 µm, permitting a resolution of more than 1,600 per square millimeter; by introducing electrical connections on a second level of a multilevel wafer, or similar techniques, the resolution of the array may be limited only by the package size and/or fabrication size of photodetectors.

With continued reference to FIG. 1, photodetectors and/or array of photodetectors may be constructed using any suitable fabrication method. Fabrication may be performed by assembling one or more electrical components and/or photodetectors in one or more circuits. Electrical components may include passive and active components, including without limitation resistors, capacitors, inductors, switches or relays, voltage sources, and the like. Electrical components may include one or more semiconductor components, such as diodes, transistors, and the like, consisting of one or more semiconductor materials, such as without limitation silicon, germanium, indium, gallium, arsenide, nitride, mercury, cadmium, and/or telluride, processed with dopants, oxidization, and ohmic connection to conducting elements such as metal leads. Some components may be fabricated separately and/or acquired as separate units and then combined with each other or with other portions of circuits to form circuits. Fabrication may depend on the nature of a component; for instance, and without limitation, fabrication of resistors may include forming a portion of a material having a known resistivity in a length and cross-sectional volume producing a desired degree of resistance, an inductor may be formed by performing a prescribed number of wire winding about a core, a capacitor may be formed by sandwiching a dielectric material between two conducting plates, and the like. Fabrication of semiconductors may follow essentially the same general process in separate and integrated components as set forth in further detail below; indeed, individual semiconductors may be grown and formed in lots using integrated circuit construction methodologies for doping, oxidization, and the like, and then cut into separate components afterwards. Fabrication of semiconductor elements, including without limitation diodes, transistors, and the like, may be achieved by performing a series of oxidization, doping, ohmic connection, material deposition, and other steps to create desired characteristics; persons skilled in the art, upon reviewing the entirety of this disclosure, will be aware of various techniques that may be applied to manufacture a given semiconductor component or device.

With continued reference to FIG. 1, one or more components and/or circuits may be fabricated together to form an integrated circuit. This may generally be achieved by growing at least a wafer of semiconductor material, doping regions of it to form, for instance, npn junctions, pnp junctions, p, n, p+, and or n+ regions, and/or other regions with local material properties, to produce components and terminals of semiconductor components such as base, gate, source and drain regions of a field-effect transistor such as a so-called metal oxide field-effect transistor (MOSFET), base, collector and emitter regions of bipolar junction BJT transistors, and the like. Common field-effect transistors include but are not limited to carbon nanotube field-effect transistor (CNFET), junction gate field-effect transistor (JFET), metal-semiconductor field-effect transistor (MESFET), high-electron-mobility transistor (HEMT), metal-oxide-semiconductor field-effect transistor (MOSFET), inverted-T field-effect transistor (ITFET), fin field-effect transistor (FinFET), fast-recovery epitaxial diode field-effect transistor (FREDFET), thin-film transistor, organic field-effect transistor (OFET), ballistic transistor, floating-gate transistor, ion-sensitive field-effect transistor (IFSET), electrolyte-oxide-semiconductor field-effect transistor (EOSFET), and/or deoxyribonucleic acid field-effect transistor (DNAFET). A person of ordinary skill in the art will be aware of various forms or categories of semiconductor devices that may be created, at least in part, by introducing dopants to various portions of a wafer. Further fabrication steps may include oxidization or other processes to create insulating layers, including without limitation at the gate of a field-effect transistor, formation of conductive channels between components, and the like. In one or more embodiments, logical components may be fabricated using combinations of transistors and the like, for instance by following a complimentary MOSFET (CMOS) process whereby desired element outputs based on element inputs are achieved using complementary circuits each achieving the desired output using active-high and active-low MOSFETS or the like. CMOS and other processes may similarly be used to produce analog components and/or components or circuits combining analog and digital circuit elements. Deposition of doping material, etching, oxidization, and similar steps may be performed by selective addition and/or removal of material using automated manufacturing devices in which a series of fabrication steps are directed at particular locations on the wafer and using particular tools or materials to perform each step; such automated steps may be directed by or derived from simulated circuits as described in further detail below.

With continued reference to FIG. 1, fabrication may include the deposition of multiple layers of wafer; as a nonlimiting example, two or more layers of wafer may be constructed according to a circuit plan or simulation which may contemplate one or more conducting connections between layers; circuits so planned may have any three-dimensional configuration, including overlapping or interlocking circuit portions, as described in further detail below. Wafers may be bound together using any suitable process, including adhesion or other processes that securely bind layers together; in some embodiments, layers are bound with sufficient firmness to make it impractical or impossible to separate layers without destroying circuits deposited thereon. Layers may be connected using vertical interconnect accesses (VIA or via), which may include, as a non-limiting example, holes drilled from a conducting channel on a first wafer to a conducting channel on a second wafer and coated with a conducting material such as tungsten or the like, so that a conducting path is formed from the channel on the first wafer to the channel on the second wafer. VIAs may also be used to connect one or more semiconductor layers to one or more conductive backing connections, such as one or more layers of conducting material etched to form desired conductive paths between components, separate from one another by insulating layers, and connected to one another and to conductive paths in wafer layers using VIAs.

With continued reference to FIG. 1, each photodetector of plurality of photodetectors may have at least a signal detection parameter. As used herein, a signal detection parameter is a parameter controlling the ability of a photodetector to detect at least a photon and/or one or more properties of a detected photon. In one or more embodiments, a signal detection parameter may determine what characteristic or characteristics at least a photon directed to the photodetector must possess to be detected. For instance, a signal detection parameter may include a wavelength and/or frequency at which a photon may be detected, a time window within which detection is possible at a particular photodetector, an angle of incidence, polarization, or other attributes or factors as described in further detail below. A signal detection parameter may include an intensity level of the at least a photon, i.e. a number of photons required to elicit a change in at least an electrical parameter in a circuit incorporating the at least a photodetector. Plurality of photodetectors may have heterogenous signal detection parameters; signal detectors and/or signal detection parameters may be heterogeneous where the plurality of photodetectors includes at least a first photodetector having a first signal detection parameter of the at least a signal detection parameter and at least a second photodetector having a second signal detection parameter of the at least a signal detection parameter, and where the at least a first signal detection parameter differs from the at least a second signal detection parameter. Heterogenous signal detection parameters may assist array in eliminating noise, increase the ability of array to detect attributes of tissue being sampled, and/or increase the temporal resolution of array.

With continued reference to FIG. 1, at least a signal detection parameter may include a temporal detection window. For the purposes of this disclosure, a temporal detection window is a period of time during which a photodetector is receptive to detection of photons, such as when an SPAD is in pre-avalanche mode as described above. Temporal detection window may be set by a delay after a given event or time, including reception of signal by another photodetector. This may be accomplished using delay circuitry. Delay circuitry may operate to set photodetector to a receptive mode at the desired time. SPADs and other similar devices have the property that the bias voltage may be dynamically adjusted such that the detector is "off" or largely insensitive to incoming photons when below breakdown voltage, and "on" or sensitive to incoming photons when above breakdown voltage. Once a current has been registered indicating photon arrival, the diode may be required to be reset via an active or passive quenching circuit. This may lead to a so-called "dead time" in which no arriving photons are counted. Varied temporal detection windows may permit a control circuit as described below to set bias voltages in a sequence corresponding to initiation of each temporal detection window, so that while one detector is quiescent, other nearby detectors are capable of receiving signals. As a nonlimiting example, a first signal detection parameter may include a first temporal detection window, a second signal detection parameter may include a second temporal detection window, and at least a portion of the first temporal detection window may not overlap with the second temporal detection window.

With continued reference to FIG. 1, delay circuitry may also block circuit transmission of signals from photodetectors that are outside their temporal detection windows, for instance by passing output of photodetectors through a Boolean "AND" gate having a second input at delay circuitry and passing a "false" value to the second input for any detector outside its temporal detection window. The increase in temporal and/or spatial resolution of a SPAD or other photodetector may have several advantages when applied to 2D or 3D imaging of biological tissue, such as the eye or other organ, based on a time-of-flight measurement device or the like. This may particularly be the case when interested in detecting time-varying signals with good spatial resolution. In a representative use, time-varying absorption of photons may be correlated to blood oxygenation. In another use, Doppler flow measurement may be more accurate in a system with greater time and/or spatial resolution. This approach may have additional utility in industrial applications e.g. automotive Lidar, where the ability to increase spatial and/or temporal resolution within all or some regions of the field of view is of interest.

With continued reference to FIG. 1, setting of receptive modes of photodetectors and/or intensity levels at which photodetectors emit detection signals may be controlled using a bias control circuit. Bias control circuit may function to set a bias of a photodetector to enable detection of some quantity of photons. In the case of SPAD detector, voltage bias of diode may be programmable in one or more steps such that the SPAD may be reverse-biased above the breakdown voltage of the junction in order to enable "Geigermode" single photon detection or biased below breakdown voltage to enable linear gain detection mode. In the case of other detector types of variable gain (e.g. PMT, MCP, MCP-MPT, photodiode, or the like), voltage bias may be programmable to enable adjustable gain. Gain may be fixed, adjusted dynamically via feedback from the incident photon flux (e.g. to avoid saturation), or via other means, e.g. lookup table or other. In an embodiment, gain may be used to determine an intensity of a detected at least a photon. Voltage bias control of the detector may be triggered via some means, such as without limitation via local delay elements such as buffer circuits, fixed or programmable or triggered by a timing reference, e.g., a reference clock edge or the like. In the case of SPAD detector, detector bias control may incorporate an active, passive or combination quenching circuit to reset the diode. Reset signal may be based on photocurrent reaching a threshold level, change in photocurrent level (e.g. via sense amplifier) or other. Detector bias control may incorporate stepwise voltage level adjustment to minimize after-pulsing and other noise sources. Detector bias control may incorporate adiabatic methods to recover energy and reduce power of a high voltage bias system. System may incorporate delay logic, which may include, without limitation, local delay elements fixed or programmable and/or controlled via other reference timing circuitry. Delay logic may incorporate feedback from the incident photon flux or via other means, such as without limitation a lookup table or other. A person of ordinary skill in the art, upon reviewing the entirety of this disclosure, will be able to identify how to select and/or implement one or more photodetectors for apparatus 100.

With continued reference to FIG. 1, apparatus 100 includes a control unit 132 communicatively connected to at least a detector 128, wherein the control unit 132 is configured to receive detected signal, identify at least an event within the detected signal, correlate the intensity of the at least an identified event with at least an attribute of the at least an identified event, and determine at least an identity of at least a translocated microbe as a function of the correlation, as described in the rest of this disclosure. For the purposes of this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device. Communicative connecting may also include indirect connections via, for example and without limitation, wireless connection, radio communication, low-power wide-area network, optical communication, magnetic, capacitive, or optical coupling, and the like. In some instances, the terminology "communicatively coupled" may be used in place of communicatively connected in this disclosure.

With continued reference to FIG. 1, in one or more embodiments, control unit 132 may include a computing device. Computing device could include any analog or digital control circuit, including an operational amplifier circuit, a combinational logic circuit, a sequential logic circuit, an application-specific integrated circuit (ASIC), a field programmable gate arrays (FPGA), or the like. Computing device may include a processor communicatively connected to a memory, as described above. Computing device may include any computing device as described in this disclosure, including without limitation a microcontroller, microprocessor, digital signal processor, and/or system on a chip as described in this disclosure. Computing device may include, be included in, and/or communicate with a mobile device such as a mobile telephone, smartphone, or tablet. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a first computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented, as a nonlimiting example, using a "shared nothing" architecture.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing. More details regarding computing devices will be described below.

With continued reference to FIG. 1, computing device may perform determinations, classification, and/or analysis steps, methods, processes, or the like as described in this disclosure using machine learning processes. A "machine learning process", as used in this disclosure, is a process that automatedly uses a body of data known as "training data" and/or a "training set" to generate an algorithm that will be performed by a processor module to produce outputs given data provided as inputs; this is in contrast to a nonmachine learning software program where the commands to be executed are determined in advance by a user and written in a programming language. A machine learning process may utilize supervised, unsupervised, lazy-learning processes and/or neural networks. More details regarding computing devices and machine learning processes will be provided below.

With continued reference to FIG. 1, in one or more embodiments, control unit 132 is configured to perform one or more of its functions using a machine learning model, as described below. In one or more embodiments, computing device may include a machine learning module to implement one or more algorithms or create one or more machine learning models to generate outputs. However, machine learning module is exemplary and may not be necessary to create one or more machine learning models and perform any machine learning described herein. In one or more embodiments, one or more machine learning models may be generated using training data. Training data may include inputs and corresponding predetermined outputs so that machine learning module may use correlations between the provided exemplary inputs and outputs to develop an algorithm and/or relationship that then allows the machine learning model to determine its own outputs for inputs. Training data may contain correlations that a machine learning process may use to model relationships between two or more categories of data elements. Exemplary inputs and outputs may come from measurements collected using standard solutions of microbe with known identities, computer simulations, user inputs, or the like, as described below. In one or more embodiments, machine learning module may obtain training data by querying a communicatively connected database that includes past inputs and outputs. Training data may include inputs from various types of databases, resources, libraries, dependencies, and/or user inputs, as well as outputs correlated to each of those inputs, so that machine learning model may determine an output. Correlations may indicate causative and/or predictive links between data, which may be modeled as relationships, such as mathematical relationships, by machine learning models, as described in further detail below. In one or more embodiments, training data may be formatted and/or organized by categories of data elements by, for example, associating data elements with one or more descriptors corresponding to categories of data elements. As a nonlimiting example, training data may include data entered in standardized forms by persons or processes, such that entry of a given data element in a given field in a form may be mapped to one or more descriptors of categories. Elements in training data may be linked to categories by tags, tokens, or other data elements. Machine learning module may be used to create at least a machine learning model using training data. Training data may be data sets that have already been converted from raw data manually, by machine, or via any other method. In some cases, the machine learning model may be trained based on user inputs. For example, user may provide user feedback to indicate that information that has been output is inaccurate, wherein machine learning model may be trained as a function of the user feedback. In some cases, machine learning model may allow for improvements to computing device, such as but not limited to an improvement relating to comparing data items, an ability to sort efficiently, an increase in accuracy of analytical methods, and the like.

With continued reference to FIG. 1, in one or more embodiments, control unit 132 may be configured to correlate the intensity of at least an identified event with at least an attribute of the at least an identified event using a machine learning model. Specifically, control unit 132 may be configured to receive pattern analysis training data comprising a plurality of training examples as inputs correlated to a plurality of event patterns as outputs, iteratively train a pattern analysis model using the pattern analysis training data, and correlating intensity of at least an identified event with at least an attribute of the at least an identified event using the trained pattern analysis model. For the purposes of this disclosure, a "training example" is a standard feature of a signal detected or simulated based on a microbe of known identity or a variant closely related thereto, capturing one or more prominent characteristics to expected from measuring a sample containing the microbe. In one or more embodiments, training examples may be embedded in one or more training signals. In one or more embodiments, training signals may include one or more signals collected using solutions of pure microbes with known identities. In one or more embodiments, training signals may include one or more simulated signals or events synthesized using a computer software such as COMSOL. Pattern analysis model may include or be implemented using any type of machine learning model or algorithm described in this disclosure. In one or more embodiments, pattern analysis model may be a neural network such as without limitation a one-dimensional convolutional neural network, a recurrent neural network, a transformer with one or more encoders and one or more decoders, a temporal convolutional network, or a deep neural network, as described below. In one or more embodiments, pattern analysis model may implement one or more feature extraction and/or feature learning algorithms, as described below. For the purposes of this disclosure, a "signal pattern" is an abstract representation of elements of portions within signal, reflecting one or more spatial relationships, attributes, or correlations therein, as described below. In one or more embodiments, signal patterns may include one or more user inputs.

With continued reference to FIG. 1, control unit 132 may be configured to perform feature extraction on one or more identified events. For the purposes of this disclosure, "feature extraction" is a process of transforming an initial data set into informative measures and values. For example, feature extraction may include a process of determining one or more geometric features of detected signal. In one or more embodiments, feature extraction may be used to determine one or more spatial relationships, attributes, or correlations within signal/peak that may be used to identify one or more microbes that contributed to the signal/peak. In one or more embodiments, control unit 132 may be configured to extract one or more regions of interest, wherein the regions of interest may be used to extract one or more features using one or more feature extraction techniques.

With continued reference to FIG. 1, control unit 132 may be configured to perform one or more of its functions, such as feature extraction, using a feature learning algorithm. For the purposes of this disclosure, a "feature learning algorithm" is a machine-learning algorithm that identifies associations between elements of data in a data set, which may include without limitation a training data set, where particular outputs and/or inputs are not specified. For instance, and without limitation, a feature learning algorithm may detect co-occurrences of elements of data, as defined above, with each other. Computing device may perform feature learning algorithm by dividing elements or sets of data into various sub-combinations of such data to create new elements of data and evaluate which elements of data tend to co-occur with which other elements. In one or more embodiments, feature learning algorithm may perform clustering of data.

With continued reference to FIG. 1, feature learning and/or clustering algorithm may be implemented, as a nonlimiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean. For the purposes of this disclosure, "cluster analysis" is a process that includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering, whereby each observation or unclassified cluster data entry belongs to a cluster or not. Cluster analysis may include soft clustering or fuzzy clustering, whereby each observation or unclassified cluster data entry belongs to each cluster to a certain degree such as for example a likelihood of belonging to a cluster; for instance, and without limitation, a fuzzy clustering algorithm may be used to identify clustering of elements of a first type or category with elements of a second type or category, and vice versa, as described below. Cluster analysis may include strict partitioning clustering, whereby each observation or unclassified cluster data entry belongs to exactly one cluster. Cluster analysis may include strict partitioning clustering with outliers, whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering, whereby observations or unclassified cluster data entries that belong to a child cluster also belong to a parent cluster.

With continued reference to FIG. 1, computing device may generate a k-means clustering algorithm receiving unclassified data and outputs a definite number of classified data entry clusters wherein the data entry clusters each contain cluster data entries. K-means algorithm may select a specific number of groups or clusters to output, identified by a variable "k". Generating k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to identify clusters of closely related data, which may be provided with user cohort labels; this may, for instance, generate an initial set of user cohort labels from an initial set of data, and may also, upon subsequent iterations, identify new clusters to be provided new labels, to which additional data may be classified, or to which previously used data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids $c_i$ of centroids in set C. Unclassified data may be assigned to a cluster based on $\text{argmin}_{c_i \ni c} \text{dist}(c_i, x)^2$, where argmin includes argument of the minimum, $c_i$ includes a collection of centroids in a set C, and dist includes standard Euclidean distance. K-means clustering module may then recompute centroids by taking mean of all cluster data entries assigned to a centroid's cluster. This may be calculated based on $c_i = 1/|S_i| \Sigma x_i \ni S_i^{xi}$. K-means clustering algorithm may continue to repeat these calculations until a stopping criterion has been satisfied such as when cluster data entries do not change clusters, the sum of the distances have been minimized, and/or some maximum number of iterations has been reached.

With continued reference to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected element. Degree of similarity index value may indicate how close a particular combination of elements is to being classified by k-means algorithm to a particular cluster. K-means clustering algorithm may evaluate the distances of the combination of elements to the k-number of clusters output by k-means clustering algorithm. Short distances between an element of data and a cluster may indicate a higher degree of similarity between the element of data and a particular cluster. Longer distances between an element and a cluster may indicate a lower degree of similarity between an element to be compared and/or clustered and a particular cluster.

With continued reference to FIG. 1, k-means clustering algorithm selects a classified data entry cluster as a function of the degree of similarity index value. In one or more embodiments, k-means clustering algorithm may select a classified data entry cluster with the smallest degree of similarity index value indicating a high degree of similarity between an element and the data entry cluster. Alternatively or additionally, k-means clustering algorithm may select a plurality of clusters having low degree of similarity index values to elements to be compared and/or clustered thereto, indicative of greater degrees of similarity. Degree of similarity index values may be compared to a threshold number indicating a minimal degree of relatedness suitable for inclusion of a set of element data in a cluster, where degree of similarity indices a-n falling under the threshold number may be included as indicative of high degrees of relatedness. The above-described illustration of feature learning using k-means clustering is included for illustrative purposes only and should not be construed as limiting potential implementation of feature learning algorithms; a person of ordinary skill in the art, upon reviewing the entirety of this disclosure, will be aware of various additional or alternative feature learning approaches, such as particle swarm optimization (PSO) and generative adversarial network (GAN) that may be used consistently with this disclosure.

With continued reference to FIG. 1, in one or more embodiments, pattern analysis model may be iteratively trained as a function of user feedback. In one or more embodiments, a user may provide feedback to pattern analysis model, such as feedback indicating incorrect identification of one or more attributes. In one or more embodiments, pattern analysis model may be iteratively updated and/or re-trained, wherein user may provide feedback following each iteration of the processing. In one or more embodiments, iteratively training pattern analysis model may allow for faster processing, optimization of computer efficiency, and the like.

With continued reference to FIG. 1, in one or more embodiments, control unit 132 may include or be configured to communicate with at least a display device while performing one or more of its functions to display one or more results via a user interface, such as a graphical user interface. In one or more embodiments, control unit 132 may be configured to communicate with display device to directly display at least a detected signal. In one or more embodiments, control unit 132 may be configured to communicate with display device to display one or more attributes and/or one or more correlations as a function of signal. In one or more embodiments, control unit 132 may be configured to communicate with display device to display at least an identity of detected microbe as a function of signal. Additional details regarding how signal is processed and how attributes therein are extracted are provided below in this disclosure. For the purposes of this disclosure, a "display device" is a computer device that is either part of control unit 132 or a secondary device separate and distinct from but communicatively connected to control unit 132. Display device may include a desktop, a laptop, a smartphone, a tablet, or the like. In one or more embodiments, display device may be communicatively connected to control unit 132 such as, for example, through network communication, through Bluetooth communication, and/or the like. In one or more embodiments, user may submit one or more user inputs through user interface, such as a graphical user interface, embedded within display device.

With continued reference to FIG. 1, for the purposes of this disclosure, a "user interface" is a means by which user and a computer system interact, for example, through the use of input devices and software. User interface may include graphical user interface (GUI), command line interface (CLI), menu-driven user interface, touch user interface, voice user interface (VUI), form-based user interface, any combination thereof, and the like. In one or more embodiments, user may interact with user interface using computing device distinct from and communicatively connected to control unit 132, such as a desktop, a laptop, a smartphone, a tablet, or the like operated by the user. User interface may include one or more graphical locator and/or cursor facilities allowing user to interact with graphical models and/or combinations thereof, for instance using a touchscreen, touchpad, mouse, keyboard, and/or other manual data entry device. For the purposes of this disclosure, a "graphical user interface" is a type of user interface that allows end users to interact with electronic devices through visual representations. In one or more embodiments, graphical user interface may include icons, menus, other visual indicators or representations (graphics), audio indicators such as primary notation, display information, and related user controls. Menu may contain a list of choices and may allow users to select one from them. A menu bar may be displayed horizontally across the screen as a pull-down menu. Menu may include a context menu that appears only when user performs a specific action. Files, programs, web pages, and the like may be represented using a small picture within graphical user interface.

With continued reference to FIG. 1, in one or more embodiments, graphical user interface may contain one or more interactive elements. For the purposes of this disclosure, an "interactive element" is an element within graphical user interface that allows for communication with control unit 132 by user. For example, and without limitation, interactive elements may include a plurality of tabs wherein selection of a particular tab, such as for example, by using a fingertip, may indicate to a system to perform a particular function and display the result through graphical user interface. In one or more embodiments, interactive element may include tabs within graphical user interface, wherein the selection of a particular tab may result in a particular function. In one or more embodiments, interactive elements may include words, phrases, illustrations, and the like to indicate a particular process that user would like system to perform. A person of ordinary skill in the art, upon reviewing the entirety of this disclosure, will be aware of various ways in which user interfaces, graphical user interfaces, and/or elements thereof may be implemented and/or used as described in this disclosure.

With continued reference to FIG. 1, in one or more embodiments, apparatus 100 may include a Faraday cage 136 that is connected to control unit 132 and encapsulates the rest of apparatus 100. For the purposes of this disclosure, a "Faraday cage" or "Faraday shield" is an enclosure used to shield what it encloses from external electric fields; in other words, apparatus 100 is electrically grounded. A Faraday shield may be formed by a continuous covering of a conductive material such as a metal, or in the case of a Faraday cage, by a mesh of such materials. Using Faraday cage 136 may ensure that apparatus 100 (and control unit 132 contained therein) performs one or more of its functions described herein without being disturbed by external electromagnetic radiation.

Figure 2A:
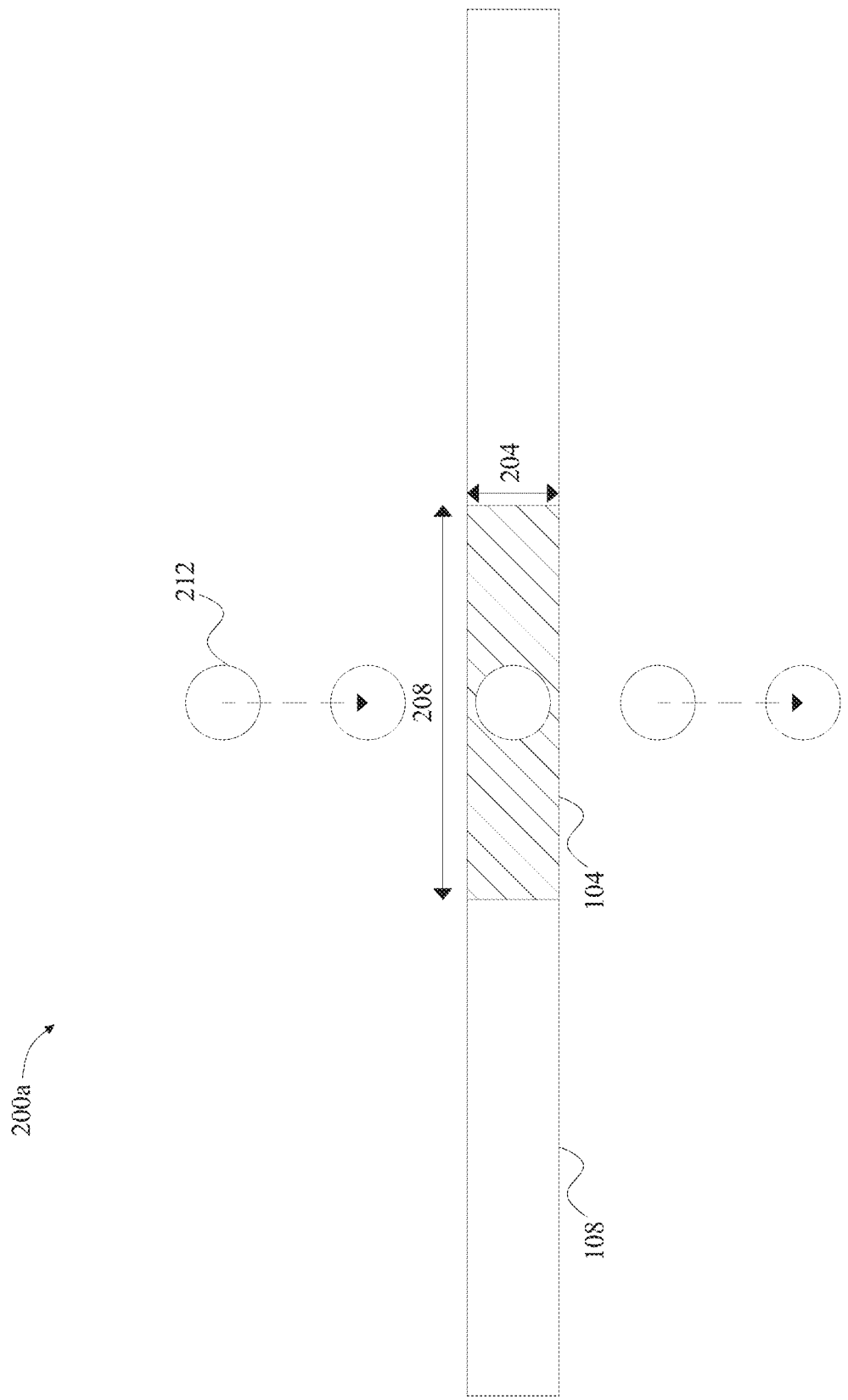
FIG. 2A is an exemplary embodiment of a cross-sectional view of a nanopore through which a microbe is translocated.

Referring now to FIG. 2A, an exemplary cross-sectional view 200a of nanopore 104 within a matrix 108 is illustrated. In one or more embodiments, nanopore 104 may be described by a geometry, as described below. For the purposes of this disclosure, a "geometry" of nanopore 104 is a three-dimensional (3D) representation of a contour of nanopore 104 in both its longitudinal and lateral directions, capturing all features (such as projections, recesses, or the like) in every angle and direction; it may be any feasible and/or applicable geometry for construction of nanopore 104 and/or use of apparatus 100, such as right or oblique circular cylinder, elliptic cylinder, right rectangular prism, right square prism, triangular prism, pentagonal prism, hexagonal prism, parallelepiped, rhombohedrum, trigonal trapezohedron, truncated sphere, truncated ellipsoid, and/or the like. In one or more embodiments, nanopore 104 may be described by two additional parameters: a longitudinal dimension (i.e., thickness) 204 and a lateral dimension 208 (i.e., size), as described above. For the purposes of this disclosure, lateral dimension 208 of nanopore 104 is the longest lateral distance from one side of an orifice to another, through a straight line. As a nonlimiting example, for nanopore 104 with a right circular cylinder geometry, lateral dimension 208 is the diameter of the circular cross section. As another nonlimiting example, for nanopore 104 with an elliptic cylinder geometry, lateral dimension 208 is the length of the major axis of the elliptical cross section. As another nonlimiting example, for nanopore 104 with a right rectangular prism geometry, lateral dimension 208 is the length of the diagonal of the rectangular cross section. As a nonlimiting example, nanopore 104 may be excavated in a membrane of polyimide with a 12.5-micrometer thickness 204 and a 4-micrometer diameter 208. As another nonlimiting example, nanopore 104 may be excavated in a wafer of fused silica with a 160-micrometer thickness 204 and a 4-micrometer diameter 208. As a nonlimiting example, nanopore 104 may be excavated from a conical cavity within thin-layer matrix 108 that tapers from one side of thin-layer matrix 108 to the other side of thin-layer matrix 108. As another nonlimiting example, nanopore 104 may be excavated from a cylindrical cavity within thin-layer matrix 108.

With continued reference to FIG. 2A, nanopore 104 may have an aspect ratio. For the purposes of this disclosure, an "aspect ratio" is a ratio between longitudinal dimension 204 and lateral dimension 208. In one or more embodiments, aspect ratio may have an impact on the selectivity of nanopore 104 and/or apparatus 100 towards microbe 212.

With continued reference to FIG. 2A, a microbe 212 may be translocated through nanopore 104. For the purposes of this disclosure, a microbe is an organism of microscopic size, which may exist in its single-celled form or as a colony of cells (except for viruses that do not have cellular structures) and may potentially function as a pathogen and infect a host to result in one or more symptoms. Microbes 212 may include viruses such as without limitation Influenzavirus, Parainfluenzavirus, Rhinovirus, Adenovirus, or Respiratory Syncytial Virus, bacteria such as without limitation *Escherichia coli, Salmonella enterica*, or *Streptococcus pyogenes*, fungi such as without limitation *Histoplasma capsulatum* or *Rhizopus oryzae*, or the like. Microbe 212 may have various sizes, shapes, and/or surface charges that interact with nanopore 104 in different manners, e.g., as a function of the size, geometry, voltage difference, and/or coating materials of the nanopore 104. For the purposes of this disclosure, a "translocation" of microbe 212 refers to the transport of the microbe 212 through nanopore 104, entering from one open end and leaving from the other. Translocation of microbe 212 may be a result of electrophoresis, diffusion, hydrostatic pressure, a combination thereof, or the like. A person of ordinary skill in the art, upon reviewing the entirety of this disclosure, may recognize the large number of parameters involved for selective detection of microbe 212 and the strategies for selecting them, as described below. In one or more embodiments, translocation of microbe 212 may result in displacement of ionic species within nanopore 104, which may cause a reduction of conductivity and results in a resistive pulse, as described below.

Figure 2B:
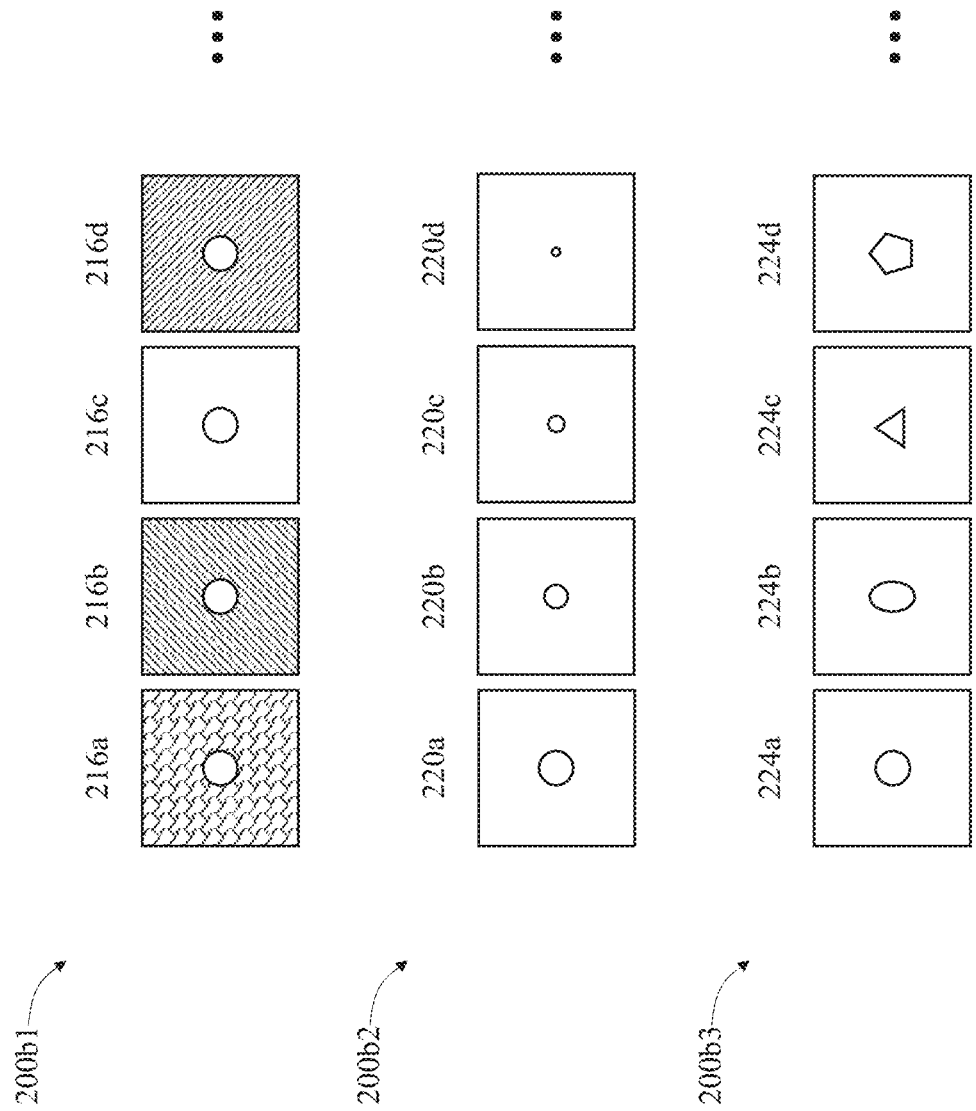
FIG. 2B is an exemplary embodiment of a plurality of nanopores arranged in a line.

Referring now to FIG. 2B, three exemplary illustrations 200b1-3 are shown for plurality of nanopores 104 arranged in a line, such as a straight line, a curved line, or a loop. Plurality of nanopores 104 may have two or more different configurations to achieve selective translocation of one or more microbes. In one or more embodiments wherein plurality of nanopores 104 is arranged in a line, as shown in 200b1, at least a first nanopore 104 within plurality of nanopores 104 may have a first voltage difference 216a along a longitudinal axis of the at least a first nanopore 104, at least a second nanopore 104 within plurality of nanopores 104 may have a second voltage difference 216b along a longitudinal axis of the at least a second nanopore, and the first voltage difference 216a is different from the second voltage difference 216b. In one or more embodiments, as shown in 200b1, each nanopore 104 within plurality of nanopores 104 may have a unique voltage difference (216a, 216b, 216c, 216d, etc., as shown in different shadings), as described above. In addition, the plurality of nanopores 104 may differ by a number of other factors. In some nonlimiting examples, they may differ based on different pressures, different pre-processing filtering mechanisms, wavelength used for detection, pore materials, and the like.

With continued reference to FIG. 2B, in one or more embodiments wherein plurality of nanopores 104 is arranged in a line, as shown in 200b2, at least a first nanopore 104 within plurality of nanopores 104 may have a first size 220a between 100 nanometers and 20 micrometers, at least a second nanopore 104 within plurality of nanopores 104 may have a second size 220b between 100 nanometers and 20 micrometers, and the first size is different from the second size. In one or more embodiments, as shown in 200b2, each nanopore 104 within plurality of nanopores 104 may have a unique size (220a, 220b, 220c, 220d, etc.) between 100 nanometers and 20 micrometers.

With continued reference to FIG. 2B, in one or more embodiments wherein plurality of nanopores 104 is arranged in a line, as shown in 200b3, at least a first nanopore 104 within plurality of nanopores 104 may have a first geometry 224a, at least a second nanopore 104 within plurality of nanopores 104 may have a second geometry 224b, and the first geometry is different from the second geometry. In one or more embodiments, as shown in 200b3, each nanopore 104 within plurality of nanopores 104 may have a unique geometry (224a, 224b, 224c, 224d, etc.).

Figure 2C:
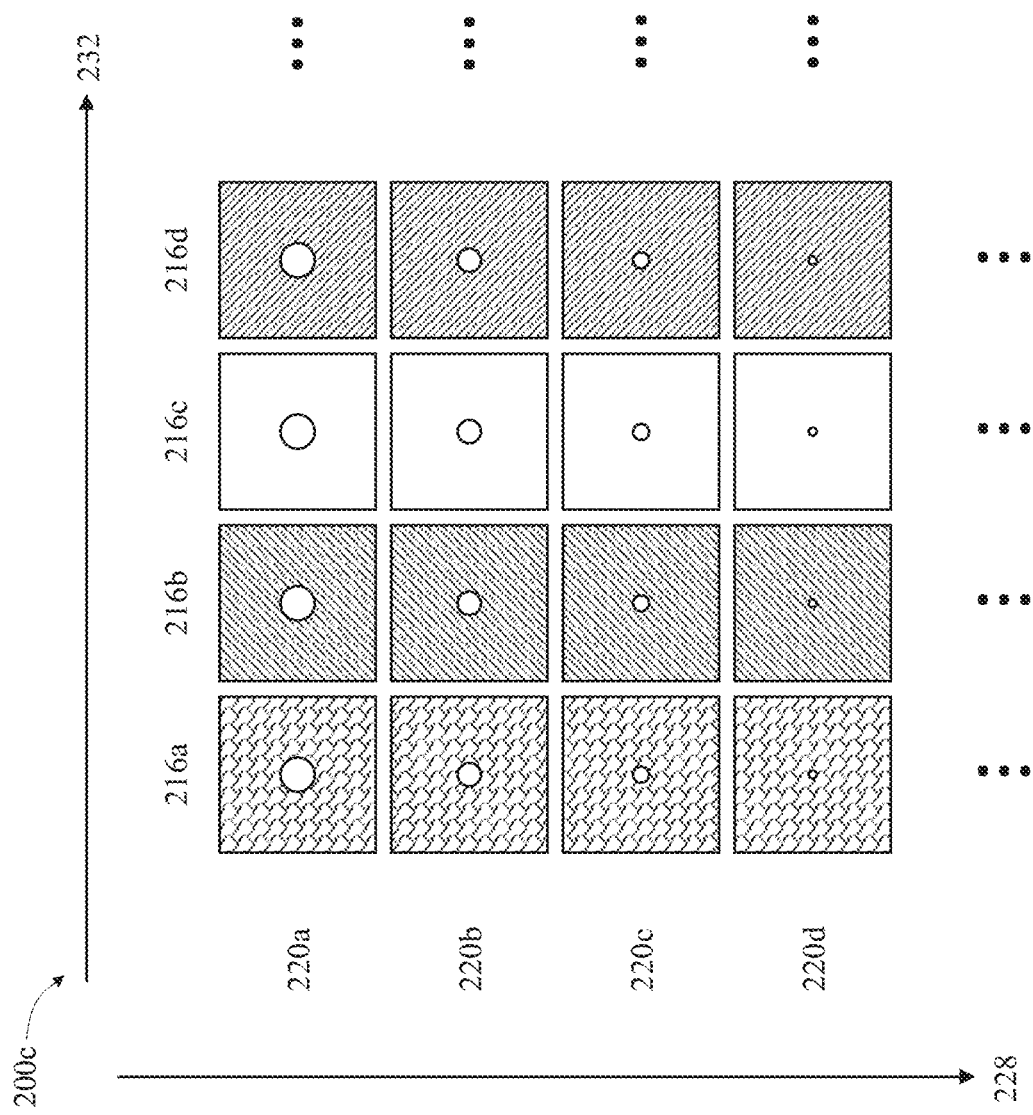
FIG. 2C is an exemplary embodiment of plurality of nanopores arranged in a two-dimensional (2D) matrix.

Referring now to FIG. 2C, an exemplary embodiment 200c for plurality of nanopores 104 arranged in a 2D array/matrix is illustrated. For the purposes of this disclosure, "2D array" and "2D matrix" are both intended to represent one or more types of geometrical arrangement and/or topology among a plurality of elements within a substantially flat plane (i.e., a plane that is apparently flat to a naked eye) and may be used interchangeably. 2D matrix 200c may be any 2D array/matrix, such as, without limitation, a square array, a rectangular array, an oblique array, a hexagonal array, or the like. A person of ordinary skill in the art, upon reviewing the entirety of this disclosure, will be recognize the various possible ways in which plurality of nanopores 104 may be arranged in 2D. In one or more embodiments, 2D matrix 200c May include at least two axes: a first axis 228 and a second axis 232, wherein the first axis 228 extends in a direction that is different from the direction in which second axis 232 extends. In some cases, first axis 228 and second axis 232 may be perpendicular to each other. In some cases, first axis 228 and second axis 232 may be joined at an angle that is not 90°. In some cases, the assignment of first vs. second axis may be arbitrary.

With continued reference to FIG. 2C, in one or more embodiments wherein nanopores 104 are arranged in 2D matrix 200c, plurality of nanopores 104 may be arranged along first axis 228, wherein at least a first nanopore 104 along the first axis 228 has a first size 220a between 100 nanometers and 20 micrometers, at least a second nanopore 104 along the first axis 228 has a second size between 100 nanometers and 20 micrometers, and the first size 220a is different from the second size 220b; plurality of nanopores 104 may be arranged along second axis 232, wherein at least a first nanopore 104 along the second axis 232 has a first voltage difference 216a along a longitudinal axis of the at least a first nanopore 104, at least a second nanopore 104 along the second axis 232 has a second voltage difference 216b along a longitudinal axis of the at least a second nanopore 104, and the first voltage difference 216a is different from the second voltage difference 216b. In one or more embodiments wherein nanopores 104 are arranged in 2D matrix 200c, plurality of nanopores 104 may be arranged along first axis 228, wherein each nanopore 104 within one or more nanopores along the first axis 228 has a unique size between 100 nanometers and 20 micrometers that is different from the size of the rest of nanopores 104 along the first axis 228; plurality of nanopores may be arranged along second axis 232, wherein each nanopore 104 within one or more nanopores along the second axis 232 has a unique voltage difference that's different from the voltage difference of the rest of nanopores along the second axis 232.

With continued reference to FIG. 2C, in one or more embodiments wherein nanopores 104 are arranged in 2D matrix 200c, at least a first nanopore 104 within plurality of nanopores 104 may have a first geometry, at least a second nanopore 104 within plurality of nanopores 104 may have a second geometry, and the first geometry is different from the second geometry, as described above for FIG. 2B. In one or more embodiments wherein nanopores 104 are arranged in 2D matrix 200c, each nanopore 104 within one or more nanopores 104 along one or more axes (such as first axis 228, second axis 232, and/or the like) may have a geometry that's different from the geometry of the rest of nanopores 104 along that axis, as described above for FIG. 2B.

With continued reference to FIG. 2A-C, nanopores 104 may be arranged in 3D matrix. In some cases, 3D matrix may be dissected into a plurality of lines 200b and/or a plurality of 2D matrices 200c, consistent with details described above. In one or more embodiments wherein plurality of nanopores 104 is arranged in 3D matrix, at least a first nanopore 104 within plurality of nanopores 104 may have a first size 220a between 100 nanometers and 20 micrometers, at least a second nanopore 104 within plurality of nanopores 104 may have a second size 220b between 100 nanometers and 20 micrometers, and the first size is different from the second size. In one or more embodiments wherein plurality of nanopores 104 is arranged in 3D matrix, each nanopore 104 within plurality of nanopores 104 may have a unique size (220a, 220b, 220c, 220d, etc.) between 100 nanometers and 20 micrometers. In one or more embodiments wherein plurality of nanopores 104 is arranged in 3D matrix, at least a first nanopore 104 within plurality of nanopores 104 may have a first voltage difference 216a along a longitudinal axis of the at least a first nanopore 104, at least a second nanopore 104 within plurality of nanopores 104 may have a second voltage difference 216b along a longitudinal axis of the at least a second nanopore, and the first voltage difference 216a is different from the second voltage difference 216b. In one or more embodiments wherein plurality of nanopores 104 is arranged in 3D matrix, each nanopore 104 within plurality of nanopores 104 may have a unique voltage difference (216a, 216b, 216c, 216d, etc.). In one or more embodiments wherein plurality of nanopores 104 is arranged in 3D matrix, at least a first nanopore 104 within plurality of nanopores 104 may have a first geometry, at least a second nanopore 104 within plurality of nanopores 104 may have a second geometry, and the first geometry is different from the second geometry. In one or more embodiments, each nanopore 104 within one or more nanopores 104 may have a geometry that's different from the geometry of the rest of nanopores 104.

With continued reference to FIG. 2A-C, it is worth noting that size 220 of nanopore 104, geometry 224 of nanopore 104, and voltage difference 216 applied to nanopore 104 are not the only tunable parameters applicable to apparatus 100. Instead, any tunable parameter that may resolve or differentiate one type of microbe 212 from another may be applied to apparatus 100, for example and without limitation, across one or more axes within a 2D array of nanopores 104. As a nonlimiting example, at least a first nanopore 104 may be applied with a first hydrostatic pressure, at least a second nanopore 104 may be applied with a second hydrostatic pressure, wherein the first hydrostatic pressure is different the second hydrostatic pressure. A person of ordinary skill in the art, upon reviewing the entirety of this disclosure, will be able to recognize additional parameters not disclosed in this application that may be applicable to apparatus 100.

Referring now to FIG. 3A, an exemplary embodiment 300a of a signal 300a is illustrated. Analyzing signal trace 300a may include extracting one or more statistical characteristics from at least a portion of the signal trace, such as a mean (i.e., average), $\mu$, or a standard deviation, $\sigma$. In one or more embodiments, detecting signal or event comprises detecting at least a flat interval 304a-c. For the purposes of this disclosure, a flat interval is an isolated, well-defined spatial or temporal region within signal trace 300a wherein the first derivative of signal trace 300a does not deviate beyond a noise threshold 308. For the purposes of this disclosure, a noise threshold is an arbitrary cutoff that equals $\sigma$ of the first derivative of entire signal trace 300a multiplied by a scaling factor. In one or more embodiments, noise threshold 308 may be equal to 1.5 times the $\sigma$ of the first derivative of entire signal trace. In one or more embodiments, for detection of bacteria, flat interval 304a-c may have a minimum temporal duration of 2 milliseconds and/or be separated from one another by at least an interval of 0.1 millisecond. In one or more embodiments, detecting at least a flat interval 304a-c may include processing signal trace 300a using a low-pass filter (e.g., a filter with a 1 kHz cutoff) first.

With continued reference to FIG. 3A, detecting signal 300a may include processing the signal 300a. For instance, apparatus 100 may analyze, modify, and/or synthesize a signal representative of data in order to improve the signal, for instance by improving transmission, storage efficiency, or signal to noise ratio. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which vary continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further nonlimiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 3A, in one or more embodiments, detecting signal 300a and/or identifying one or more events therein comprises selecting an eligible period. For the purposes of this disclosure, an "eligible period" is a longer period of time during which signal trace 300a is generally stable (i.e., characterized by a stable baseline 312) and therefore worth looking for one or more signals; operationally, eligible period may be a period between two flanking, back-to-back flat intervals 304a-c and characterized by a very similar average from each of the flanking flat interval 304a-c. In one or more embodiments, the two flanking flat intervals 304a-c of eligible period may each have an average that is within +/−five times the expected noise of each other. For the purposes of this disclosure, an "expected noise" is the maximum deviation of signal trace 300a from its average within flat interval 304a-c. In one or more embodiments, the mean and standard deviation of each of the flanking intervals 304a-c may be further condensed to describe an entire eligible period. As a nonlimiting example, the mean of eligible period, $\mu^e$, may be an average between the mean of the left flanking interval, $\mu_L$, and mean of the right flanking interval, $\mu_R$, whereas the standard deviation of eligible period, $\sigma_e$, may be the larger value between the standard deviation of the left flanking interval, ØL, and standard deviation of the right flanking interval, $\sigma_R$.

Referring now to FIG. 3B, an exemplary embodiment 300b for an identified event 316, as described above, within signal 300a is illustrated. In one or more embodiments, event 316 may have a minimum height (i.e., detection threshold) 320 of 5× de in order to be isolated from noise. As a nonlimiting example, for the case of a resistive pulse, as described above, event 316 may originally extend in a negative direction (i.e., as a dip) and need to be negated (i.e., flipped across the x axis) into a peak for further processing. In one or more embodiments, event 316 may include a start 324 and an end 328, the difference between which is the duration/width of the event 316, as described below. As a nonlimiting example, event 316 may have a duration/width between 0.2 milliseconds and 4 milliseconds. In one or more embodiments, event 316 may include a plurality of attributes that describe fine features of the event 316 from different perspectives, as described below.

Referring now to FIG. 3C, an exemplary embodiment 300c of several attributes that may be used to describe event 316 are illustrated. In one or more embodiments, event 316 may be described by a height attribute 332, as described above. For the purposes of this disclosure, a "height attribute" is an indicator that marks a maximum deviation of signal trace 300a from $\mu_e$; "height attribute" and "intensity" may be used interchangeably throughout this disclosure. In one or more embodiments, event 316 may be described by a width attribute 336. For the purposes of this disclosure, a "width attribute" is an indicator that indicates a spatial or temporal span of event 316 based on detection threshold 320, as described above. In one or more embodiments, event 316 may be described by an area-under-the-curve attribute (AUC) 340. For the purposes of this disclosure, an "area-under-the-curve attribute" is an indicator that indicates an actual area beneath event 316 (i.e., the shaded area in FIG. 3C, which may be determined by performing an integral within spatial or temporal span of event 316) normalized with respect to a rectangular area defined by a product of height attribute 332 and width attribute 336. In one or more embodiments, event 316 may be described by an asymmetry attribute. For the purposes of this disclosure, an "asymmetry attribute" is an indicator that indicates a relative timestamp regarding where event 316 peaks at; it is reported as a ratio of a portion 344 of width attribute 336 wherein event 316 is ascending, with respect to the width attribute 336 of the entire event 316. As a nonlimiting example, when event 316 is symmetrical, asymmetry attribute has a benchmark value equal to 0.5; an asymmetry indicator smaller than 0.5 indicates that event 316 is skewed towards its right shoulder, whereas an asymmetry indicator larger than 0.5 indicates that event 316 is skewed towards its left shoulder instead. In one or more embodiments, event 316 may be described by a number-of-peaks attribute. For the purposes of this disclosure, a "number-of-peaks attribute" is the number of times event 316 rises above a peak threshold 348 near its peak value. As a nonlimiting example, peak threshold 348 may be set as 85% with respect to height 332. In one or more embodiments, determining number-of-peaks attribute may involve a determination of the number of peaks or troughs within event 316, which may be accomplished by calculating the first derivative of the signal and determining the number of times the first derivative switches from positive to negative (for peaks) and/or from negative to positive (for troughs). In one or more embodiments, these and other features may be extracted after passing signal 300a through one or more low-pass, high-pass, and/or band-pass filters. Additionally and/or alternatively, in one or more embodiments, other attributes besides those listed above, such as peak-to-peak or trough-to-trough distance, frequency, absorbance, light attenuation at one or more wavelengths, or the like, may be used to describe the shape of event 316. In one or more embodiments, at least part of event 316 may be converted using a fast Fourier transform (FFT), Z-transform, Laplace transform, or the like, from a time domain to a frequency domain, wherein the at least part of event 316 may be dissected into a plurality of individual sine wave signals at different frequencies, and/or with different amplitudes, for further analysis and/or extraction of features; this transform may be accomplished with one or more machine learning models, as described in this disclosure; in one or more embodiments, the transformed signal may be reverse-transformed to the time domain, after operations have been performed in the latent domain. A person of ordinary skill in the art, upon reviewing the entirety of this disclosure, will be able to recognize suitable attributes when analyzing event 316.

Figure 3D:
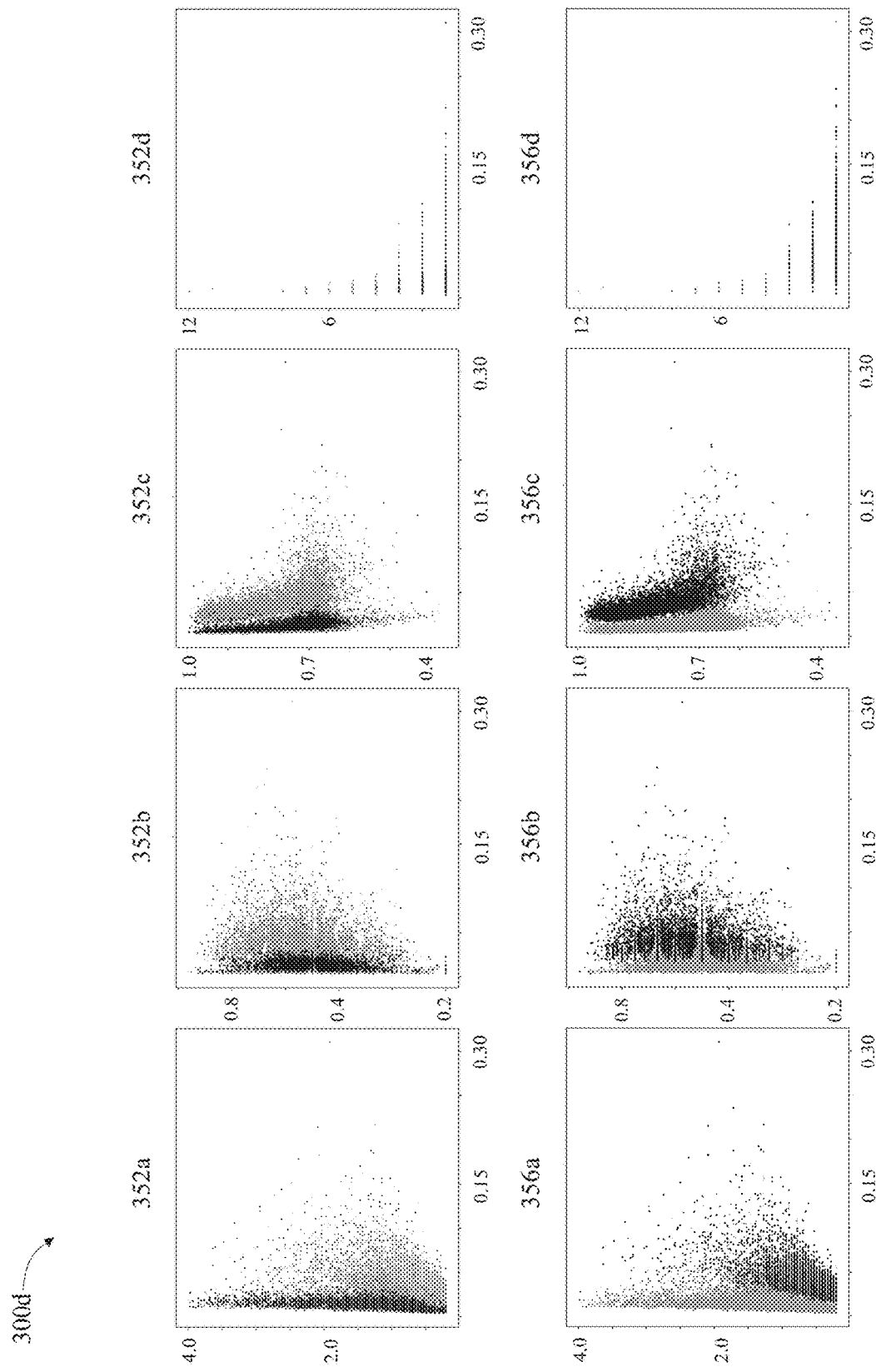
FIG. 3D are exemplary embodiments of correlations between the height attribute and other attributes of an identified event.

Referring now to FIG. 3D, nonlimiting examples of correlations 300d between peak height 332 (horizontal axis) and another attribute (height attribute 332, width attribute 336, area-under-the-curve attribute 340, asymmetry attribute, and number-of-peaks attribute vertical axis) are illustrated; axis titles are omitted for clarity and will be described below. Attributes of event 316, as described in FIG. 3C, when examined either individually or in combination, may reveal features unique to microbe 212 and facilitate detection thereof. Plots 352a-d show correlations between height attribute 332 and another attribute for *Escherichia coli*, whereas plots 356a-d show correlations between height attribute 332 and another attribute for *Salmonella enterica*. Each data point in FIG. 3D represents a detected bacterium, and its corresponding coordinates represent a height attribute 332 (horizontal axis) correlated to another attribute (vertical axis). Specifically, 352a and 356a are correlations between peak height 332 and width attribute 336; 352b and 356b are correlations between peak height 332 and asymmetry attribute; 352c and 356c are correlations between peak height 332 and area-under-the-curve attribute 340; 352d and 356d are correlations between peak height 332 and number-of-peaks attribute. As the number of detected microbes 212 increases, different clustering patterns of data points were observed for *Escherichia coli* and *Salmonella enterica*; this difference may be a result of different sizes, different shapes, and/or different surface charges of *Escherichia coli* vs *Salmonella enterica*, which results in different transport behaviors when a bacterium of either type travels through nanopore 104.

With continued reference to FIG. 3D, apparatus 100 may increase its certainty of detection by increasing the number of detected microbes 212. As a nonlimiting example, detection of a single microbe 212 may have a 70% certainty, which may not be satisfactory enough for medical applications; however, assuming a binomial distribution of probability, after the detection of 11 microbes, the probability of a correct classification increases to 92.2%; after detection of 51 microbes, this probability further increases to 99.86%; after detection of 100+ microbes, this probability will be virtually 100%. In addition, plurality of nanopores 104 of different sizes 220, geometries 224, and/or voltage differences 216, as described above, when used in parallel, may also increase the certainty of detection, particularly for a mixture of microbes 212 of various types that may be more challenging to isolate and/or detect.

With continued reference to FIG. 3A-D, in one or more embodiments wherein apparatus 100 includes plurality of nanopores 104, apparatus 100 may benefit from the multiplicity of the nanopores 104 by analyzing a plurality of signals 300*a* collected from different nanopores 104 simultaneously. A combined use of multiple nanopores 104 may result in a synergistic effect for the purpose of microbe identification. For example, and without limitation, when a first microbe 212 and a second microbe 212 are the only two microbes 212 capable of translocating through either a first nanopore 104 or a second nanopore 104, attributes of events 316 that they trigger may be indistinguishable. In some cases, it is by integrating height 332 of a first event 316 collected from first nanopore 104 and one or more attributes of a second event 316 collected from second nanopore 104 that one may reliably identify two microbes 212 from each other.

With continued reference to FIG. 3A-D, signal 300*a* and/or event 316 may be either positive or negative, and similar synergies may arise from either type of signal 300*a* and/or event 316. Benefitting from the fact that some microbes 212 may not cross certain nanopores 104 under certain applied conditions, an absence of event 316 in some nanopores 104 may provide useful information that facilitates identification of microbe 212. For example, and without limitation, while both first microbe 212 and second microbe 212 may cross first nanopore 104, producing identically shaped events 316, only second microbe 212 may be able to cross second nanopore 104. It may be only by considering both signals 300*a* and/or events 316 collected from both nanopores 104 simultaneously that one can reliably identify two microbes 212.

With continued reference to FIG. 3A-D, it is noteworthy that, while the computational pipeline may need to be performed by comparing signals 300*a* from multiple nanopores 104 simultaneously, signals 300*a* do not have to be recorded at the same time. For example, and without limitation, if a user has access to a single nanopore reader 116, the user may analyze a clinical sample multiple times by switching nanopore 104 and/or a condition applied thereto each time, as described above, thus effectively "simulating" a multiple-nanopore reader 116 in a serial rather than parallel fashion. Once recordings have been collected sequentially, the processing of all signals 300*a* may be carried out simultaneously to benefit from the synergy described above. Overall, apparatus 100 with plurality of nanopores 104, wherein the interpretation of event 316 in one nanopore 104 is conditioned by events 316 present in or absent from other nanopores 104, may have a significant advantage compared to single-nanopore designs.

With continued reference to FIG. 3A-D, it is worth noting that exemplary embodiments described herein are not the only possible ways to process signal 300*a*, identify events 316, and/or generate correlations. As a nonlimiting example, apparatus 100 may be configured to create embeddings for an entire signal trace 300*a* and extract one or more features therefrom using one or more classifiers, as described in this disclosure. A person of ordinary skill in the art, upon reviewing the entirety of this disclosure, will recognize additional variations of methods used herein for signal processing.

Figure 4:
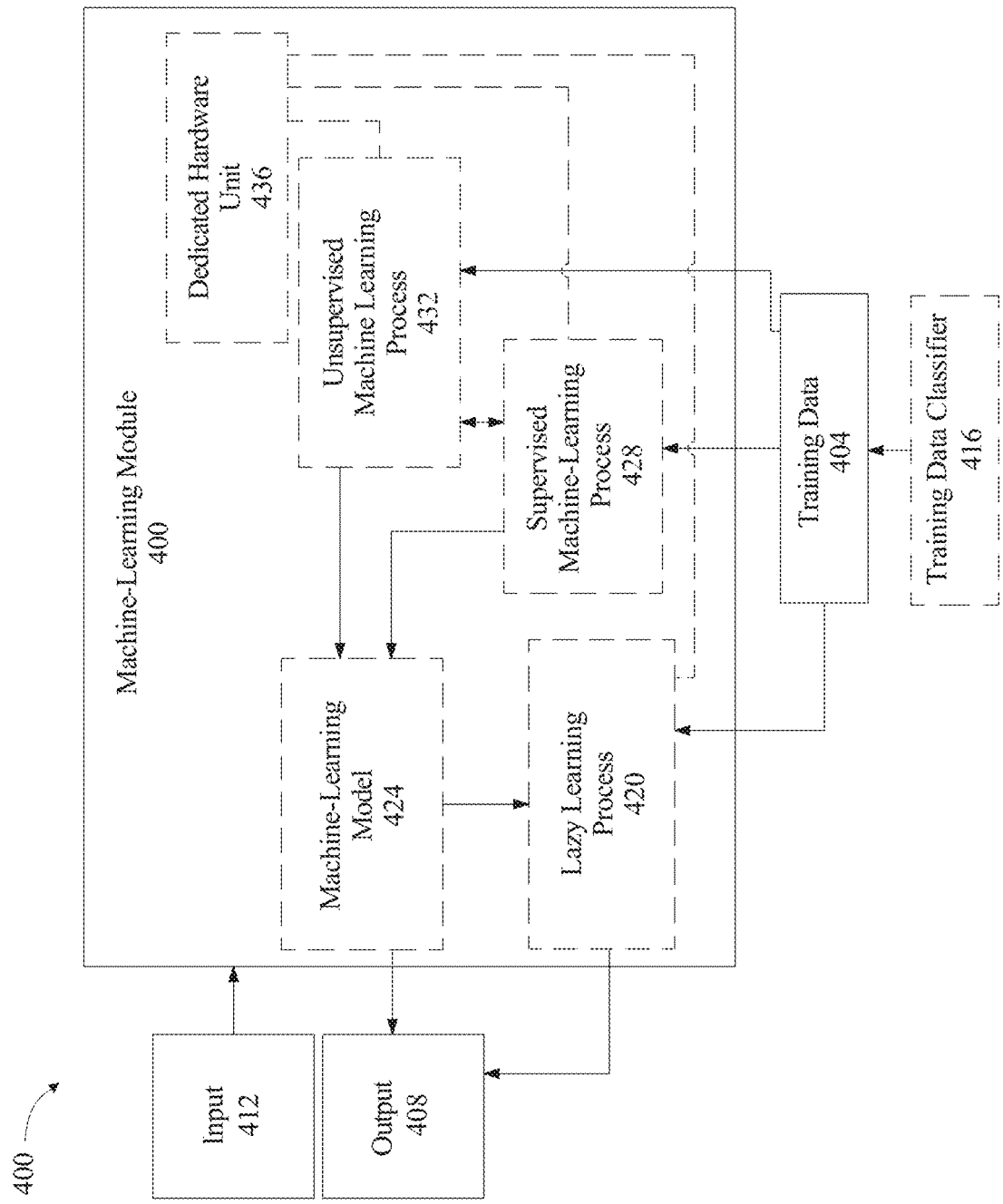
FIG. 4 is a block diagram of an exemplary embodiment of a machine learning process.

Referring now to FIG. 4, an exemplary embodiment of a machine learning module 400 that may perform one or more machine learning processes as described above is illustrated. Machine learning module may perform determinations, classification, and/or analysis steps, methods, processes, or the like as described in this disclosure using machine learning processes. For the purposes of this disclosure, a "machine learning process" is an automated process that uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are pre-determined by user and written in a programming language.

With continued reference to FIG. 4, "training data", for the purposes of this disclosure, are data containing correlations that a machine learning process may use to model relationships between two or more categories of data elements. For instance, and without limitation, training data 404 may include a plurality of data entries, also known as "training examples", each entry representing a set of data elements that were recorded, received, and/or generated together. Data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine learning processes as described in further detail below. Training data 404 may be formatted and/or organized by categories of data elements, for instance by associating data elements with one or more descriptors corresponding to categories of data elements. As a nonlimiting example, training data 404 may include data entered in standardized forms by persons or processes, such that entry of a given data element within a given field in a given form may be mapped to one or more descriptors of categories. Elements in training data 404 may be linked to descriptors of categories by tags, tokens, or other data elements. For instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

With continued reference to FIG. 4, alternatively or additionally, training data 404 may include one or more elements that are uncategorized; that is, training data 404 may not be formatted or contain descriptors for some elements of data. Machine learning algorithms and/or other processes may sort training data 404 according to one or more categorizations using, for instance, natural language processing algorithms, tokenization, detection of correlated values in raw data, and the like; categories may be generated using correlation and/or other processing algorithms. As a nonlimiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 404 to be made applicable for two or more distinct machine learning algorithms as described in further detail below. Training data 404 used by machine learning module 400 may correlate any input data as described in this disclosure to any output data as described in this disclosure. As a nonlimiting illustrative example, inputs may include inputs such as training signals and the like, and outputs may include outputs such as one or more correlations between attributes and extracted features or patterns therefrom.

With continued reference to FIG. 4, training data 404 may be filtered, sorted, and/or selected using one or more supervised and/or unsupervised machine learning processes and/or models as described in further detail below; such processes and/or models may include without limitation a training data classifier 416. For the purposes of this disclosure, a "classifier" is a machine learning model, such as a data structure representing and/or using a mathematical model, neural net, or a program generated by a machine learning algorithm, known as a "classification algorithm", that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Euclidean norm. Machine learning module 400 may generate a classifier using a classification algorithm. For the purposes of this disclosure, a "classification algorithm" is a process wherein a computing device and/or any module and/or component operating therein derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, training data classifier 416 may classify elements of training data to geographic locations, occupations, industries, and/or the like.

With continued reference to FIG. 4, machine learning module 400 may be configured to generate a classifier using a naive Bayes classification algorithm. Naive Bayes classification algorithm generates classifiers by assigning class labels to problem instances, represented as vectors of element values. Class labels are drawn from a finite set. Naive Bayes classification algorithm may include generating a family of algorithms that assume that the value of a particular element is independent of the value of any other element, given a class variable. Naive Bayes classification algorithm may be based on Bayes Theorem expressed as $P(A/B)=P(B/A)\times P(A)\div P(B)$, where $P(A/B)$ is the probability of hypothesis A given data B, also known as posterior probability; $P(B/A)$ is the probability of data B given that the hypothesis A was true; $P(A)$ is the probability of hypothesis A being true regardless of data, also known as prior probability of A; and $P(B)$ is the probability of the data regardless of the hypothesis. A naive Bayes algorithm may be generated by first transforming training data into a frequency table. Machine learning module 400 may then calculate a likelihood table by calculating probabilities of different data entries and classification labels. Machine learning module 400 may utilize a naive Bayes equation to calculate a posterior probability for each class. A class containing the highest posterior probability is the outcome of prediction. Naive Bayes classification algorithm may include a gaussian model that follows a normal distribution. Naive Bayes classification algorithm may include a multinomial model that is used for discrete counts. Naive Bayes classification algorithm may include a Bernoulli model that may be utilized when vectors are binary.

With continued reference to FIG. 4, machine learning module 400 may be configured to generate a classifier using a k-nearest neighbors (KNN) algorithm. For the purposes of this disclosure, a "k-nearest neighbors algorithm" is or at least includes a classification method that utilizes feature similarity to analyze how closely out-of-sample features resemble training data 404 and to classify input data to one or more clusters and/or categories of features as represented in training data 404; this may be performed by representing both training data 404 and input data in vector forms and using one or more measures of vector similarity to identify classifications within training data 404 and determine a classification of input data. K-nearest neighbors algorithm may include specifying a k-value, or a number directing the classifier to select the k most similar entries of training data 404 to a given sample, determining the most common class of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a nonlimiting example, an initial heuristic may include a ranking of associations between inputs 412 and elements of training data 404. Heuristic may include selecting some number of highest-ranking associations and/or training data elements.

With continued reference to FIG. 4, generating k-nearest neighbors algorithm may generate a first vector output containing a data entry cluster, generating a second vector output containing input data, and calculate the distance between the first vector output and the second vector output using any suitable norm such as cosine similarity, Euclidean distance measurement, or the like. Each vector output may be represented, without limitation, as an n-tuple of values, where n is at least 2. Each value of n-tuple of values may represent a measurement or other quantitative value associated with a given category of data or attribute, examples of which are provided in further detail below. A vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent when their directions and/or relative quantities of values are the same; thus, as a nonlimiting example, a vector represented as [5, 10, 15] may be treated as equivalent, for the purposes of this disclosure, as a vector represented as [1, 2, 3]. Vectors may be more similar where their directions are more similar, and more different where their directions are more divergent. However, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized", or divided by a "length" attribute, such as a length attribute 1 as derived using a Pythagorean norm:

$$l = \sqrt{\sum_{i=0}^{n} a_i^2},$$

where $a_i$ is attribute number of vector i. Scaling and/or normalization may function to make vector comparison independent of absolute quantities of attributes, while preserving any dependency on similarity of attributes. This may, for instance, be advantageous where cases represented in training data 404 are represented by different quantities of samples, which may result in proportionally equivalent vectors with divergent values.

With continued reference to FIG. 4, training examples for use as training data may be selected from a population of potential examples according to cohorts relevant to an analytical problem to be solved, a classification task, or the like. Alternatively or additionally, training data 404 may be selected to span a set of likely circumstances or inputs for a machine learning model and/or process to encounter when deployed. For instance, and without limitation, for each category of input data to a machine learning model and/or process that may exist in a range of values in a population of phenomena such as images, user data, process data, physical data, or the like, a computing device, control unit 132, and/or machine learning module 400 may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to user, so that a process can detect, automatically or via user input, one or more values that are not included in the set of training examples. Computing device, control unit 132, and/or machine learning module 400 may automatically generate a missing training example. This may be done by receiving and/or retrieving a missing input and/or output value and correlating the missing input and/or output value with a corresponding output and/or input value collocated in a data record with the retrieved value, provided by user, another device, or the like.

With continued reference to FIG. 4, computing device, control unit 132, and/or machine learning module 400 may be configured to preprocess training data 404. For the purposes of this disclosure, "preprocessing" training data is a process that transforms training data from a raw form to a format that can be used for training a machine learning model. Preprocessing may include sanitizing, feature selection, filtering (low-pass, high-pass, band-pass or any combination of multiple filters), operations in the Fourier/Laplace/Z-domain (i.e., transforming the trace, applying the operation, and reverse-transforming to the time domain), feature scaling, data augmentation and the like.

With continued reference to FIG. 4, computing device, control unit 132, and/or machine learning module 400 may be configured to sanitize training data. For the purposes of this disclosure, "sanitizing" training data is a process whereby training examples that interfere with convergence of a machine learning model and/or process are removed to yield a useful result. For instance, and without limitation, a training example may include an input and/or output value that is an outlier from typically encountered values, such that a machine learning algorithm using the training example will be skewed to an unlikely range of input 412 and/or output 408; a value that is more than a threshold number of standard deviations away from an average, mean, or expected value, for instance, may be eliminated. Alternatively or additionally, one or more training examples may be identified as having poor-quality data, where "poor-quality" means having a signal-to-noise ratio below a threshold value. In one or more embodiments, sanitizing training data may include steps such as removing duplicative or otherwise redundant data, interpolating missing data, correcting data errors, standardizing data, identifying outliers, and/or the like. In one or more embodiments, sanitizing training data may include algorithms that identify duplicate entries or spell-check algorithms.

With continued reference to FIG. 4, in one or more embodiments, images used to train an image classifier or other machine learning model and/or process that takes images as inputs 412 or generates images as outputs 408 may be rejected if image quality is below a threshold value. For instance, and without limitation, computing device, control unit 132, and/or machine learning module 400 may perform blur detection. Elimination of one or more blurs may be performed, as a nonlimiting example, by taking Fourier transform or a Fast Fourier Transform (FFT) of image and analyzing a distribution of low and high frequencies in the resulting frequency-domain depiction of the image. Numbers of high-frequency values below a threshold level may indicate blurriness. As a further nonlimiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of image, based on the hypothesis that rapid changes indicate sharp edges in the image, and thus are indicative of a lower degree of blurriness. Blur detection may be performed using a wavelet-based operator, which uses coefficients of a discrete wavelet transform to describe the frequency and spatial content of images. Blur detection may be performed using statistics-based operators that take advantage of several image statistics as texture descriptors in order to compute a focus level. Blur detection may be performed by using discrete cosine transform (DCT) coefficients in order to compute a focus level of an image from its frequency content.

With continued reference to FIG. 4, computing device, control unit 132, and/or machine learning module 400 may be configured to precondition one or more training examples. For instance, and without limitation, where a machine learning model and/or process has one or more inputs 412 and/or outputs 408 requiring, transmitting, or receiving a certain number of bits, samples, or other units of data, one or more elements of training examples to be used as or compared to inputs 412 and/or outputs 408 may be modified to have such a number of units of data. In one or more embodiments, computing device, control unit 132, and/or machine learning module 400 may convert a smaller number of units, such as in a low pixel count image, into a desired number of units by upsampling and interpolating. As a nonlimiting example, a low pixel count image may have 100 pixels, whereas a desired number of pixels may be 132. Control unit 132 may interpolate the low pixel count image to convert 100 pixels into 132 pixels. It should also be noted that one of ordinary skill in the art, upon reading the entirety of this disclosure, would recognize the various methods to interpolate a smaller number of data units such as samples, pixels, bits, or the like to a desired number of such units. In one or more embodiments, a set of interpolation rules may be trained by sets of highly detailed inputs 412 and/or outputs 408 and corresponding inputs 412 and/or outputs 408 downsampled to smaller numbers of units, and a neural network or another machine learning model that is trained to predict interpolated pixel values using the training data 404. As a nonlimiting example, a sample input 412 and/or output 408, such as a sample picture, with sample-expanded data units (e.g., pixels added between the original pixels) may be input to a neural network or machine learning model and output a pseudo replica sample picture with dummy values assigned to pixels between the original pixels based on a set of interpolation rules. As a nonlimiting example, in the context of an image classifier, a machine learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, computing device, control unit 132, and/or machine learning module 400 may utilize sample expander methods and/or a filter of any time (low-pass, high-pass, band-pass or any combination of multiple filters). For the purposes of this disclosure, a "low-pass filter" is a filter that passes signals with a frequency lower than a selected cutoff frequency and attenuates signals with frequencies higher than the cutoff frequency. Exemplary types of filters may include, without limitation, Chebyshev filter, Butterworth filter, Bessel filter, and elliptic filter. In one or more embodiments, filter may be a digital filter. For the purposes of this disclosure, a "digital filter" is a system used in signal processing that performs mathematical operations on a sampled, discrete-time signal to reduce or enhance certain aspects of that signal; it is in contrast to the other major type of electronic filter, the analog filter, which is typically an electronic circuit operating on continuous-time analog signals. Digital filter may include, for example and without limitation, finite impulse response (FIR) filters and infinite impulse response (IIR) filters, the latter of which contain feedback loops. Alternatively and/or additionally, filter may be an adaptive filter such as, without limitation, least-squares, least mean squares, or Kalman filter, which may potentially contain an expanded set of filtering functions and may be trained using training data similar to pattern analysis training data described above in this disclosure. The exact frequency response of the filter depends on the filter design. Computing device, control unit 132, and/or machine learning module 400 may use averaging, such as luma or chroma averaging in images, to fill in data units in between original data units.

With continued reference to FIG. 4, in one or more embodiments, computing device, control unit 132, and/or machine learning module 400 may downsample elements of a training example to a desired lower number of data elements. As a nonlimiting example, a high pixel count image may contain 256 pixels, however a desired number of pixels may be 132. Control unit 132 may downsample the high pixel count image to convert 256 pixels into 132 pixels. In some embodiments, control unit 132 may be configured to perform downsampling on data. Downsampling, also known as decimation, may include removing every $N^{th}$ entry in a sequence of samples, all but every $N^{th}$ entry, or the like, which is a process known as "compression" and may be performed, for instance by an N-sample compressor implemented using hardware or software. Anti-aliasing and/or anti-imaging filters, and/or low-pass filters, may be used to eliminate side effects of compression.

With continued reference to FIG. 4, feature selection may include narrowing and/or filtering training data 404 to exclude features and/or elements, or training data including such elements that are not relevant to a purpose for which a trained machine learning model and/or algorithm is being trained, and/or collection of features, elements, or training data including such elements based on relevance to or utility for an intended task or purpose for which a machine learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, wherein a difference between each value, X, and a minimum value, $X_{min}$, in a set or subset of values is divided by a range of values, $X_{max}$-$X_{min}$, in the set or subset:

$$X_{new} = \frac{X - X_{min}}{X_{max} - X_{min}}.$$

Feature scaling may include mean normalization, wherein a difference between each value, X, and a mean value of a set and/or subset of values, $X_{mean}$, is divided by a range of values, $X_{max}$-$X_{min}$, in the set or subset:

$$X_{new} = \frac{X - X_{mean}}{X_{max} - X_{min}}.$$

Feature scaling may include standardization, wherein a difference between X and $X_{mean}$ is divided by a standard deviation, $\sigma$, of a set or subset of values:

$$X_{new} = \frac{X - X_{mean}}{\sigma}.$$

Feature scaling may be performed using a median value of a set or subset, $X_{median}$, and/or interquartile range (IQR), which represents the difference between the 25th percentile value and the 50th percentile value (or closest values thereto by a rounding protocol), such as:

$$X_{new} = \frac{X - X_{median}}{IQR}.$$

A Person of ordinary skill in the art, upon reviewing the entirety of this disclosure, will be aware of various alternative or additional approaches that may be used for feature scaling.

With continued reference to FIG. 4, computing device, control unit 132, and/or machine learning module 400 may be configured to perform one or more processes of data augmentation. For the purposes of this disclosure, "data augmentation" is a process that adds data to a training data 404 using elements and/or entries already in the dataset. Data augmentation may be accomplished, without limitation, using interpolation, generation of modified copies of existing entries and/or examples, and/or one or more generative artificial intelligence (AI) processes, for instance using deep neural networks and/or generative adversarial networks. Generative processes may be referred to alternatively in this context as "data synthesis" and as creating "synthetic data". Augmentation may include performing one or more transformations on data, such as geometric, color space, affine, brightness, cropping, and/or contrast transformations of images.

With continued reference to FIG. 4, machine learning module 400 may be configured to perform a lazy learning process and/or protocol 420. For the purposes of this disclosure, a "lazy learning" process and/or protocol is a process whereby machine learning is conducted upon receipt of input 412 to be converted to output 408 by combining the input 412 and training data 404 to derive the algorithm to be used to produce the output 408 on demand. A lazy learning process may alternatively be referred to as a "lazy loading" or "call-when-needed" process and/or protocol. For instance, an initial set of simulations may be performed to cover an initial heuristic and/or "first guess" at an output 408 and/or relationship. As a nonlimiting example, an initial heuristic may include a ranking of associations between inputs 412 and elements of training data 404. Heuristic may include selecting some number of highest-ranking associations and/or training data 404 elements. Lazy learning may implement any suitable lazy learning algorithm, including without limitation a k-nearest neighbors algorithm, a lazy I Bayes algorithm, or the like. A person of ordinary skill in the art, upon reviewing the entirety of this disclosure, will be aware of various lazy learning algorithms that may be applied to generate outputs as described in this disclosure, including without limitation lazy learning applications of machine learning algorithms as described in further detail below.

With continued reference to FIG. 4, alternatively or additionally, machine learning processes as described in this disclosure may be used to generate machine learning models 424. A "machine learning model", for the purposes of this disclosure, is a data structure representing and/or instantiating a mathematical and/or algorithmic representation of a relationship between inputs 412 and outputs 408, generated using any machine learning process including without limitation any process described above, and stored in memory. An input 412 is submitted to a machine learning model 424 once created, which generates an output 408 based on the relationship that was derived. For instance, and without limitation, a linear regression model, generated using a linear regression algorithm, may compute a linear combination of input data using coefficients derived during machine learning processes to calculate an output datum. As a further nonlimiting example, a machine learning model 424 may be generated by creating an artificial neural network, such as a convolutional neural network comprising an input layer of nodes, one or more intermediate layers, and an output layer of nodes. Connections between nodes may be created by training the network, in which elements from a training data 404 are applied to the input nodes, and a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, as described in detail below.

With continued reference to FIG. 4, machine learning module 400 may perform at least a supervised machine learning process 428. For the purposes of this disclosure, a "supervised" machine learning process is a process with algorithms that receive training data 404 relating one or more inputs 412 to one or more outputs 408, and seek to generate one or more data structures representing and/or instantiating one or more mathematical relations relating input 412 to output 408, where each of the one or more mathematical relations is optimal according to some criterion specified to the algorithm using some scoring function. For instance, a supervised learning algorithm may include training signals and/or the like as described above as inputs, correlations between attributes as outputs, and a scoring function representing a desired form of relationship to be detected between inputs 412 and outputs 408. Scoring function may, for instance, seek to maximize the probability that a given input 412 and/or combination thereof is associated with a given output 408 to minimize the probability that a given input 412 is not associated with a given output 408. Scoring function may be expressed as a risk function representing an "expected loss" of an algorithm relating inputs 412 to outputs 408, where loss is computed as an error function representing a degree to which a prediction generated by the relation is incorrect when compared to a given input-output pair provided in training data 404. Supervised machine learning processes may include classification algorithms as defined above. A person of ordinary skill in the art, upon reviewing the entirety of this disclosure, will be aware of various possible variations of at least a supervised machine learning process 428 that may be used to determine a relation between inputs and outputs.

With continued reference to FIG. 4, training a supervised machine learning process may include, without limitation, iteratively updating coefficients, biases, and weights based on an error function, expected loss, and/or risk function. For instance, an output 408 generated by a supervised machine learning model 428 using an input example in a training example may be compared to an output example from the training example; an error function may be generated based on the comparison, which may include any error function suitable for use with any machine learning algorithm described in this disclosure, including a square of a difference between one or more sets of compared values or the like. Such an error function may be used in turn to update one or more weights, biases, coefficients, or other parameters of a machine learning model through any suitable process including without limitation gradient descent processes, least-squares processes, and/or other processes described in this disclosure. This may be done iteratively and/or recursively to gradually tune such weights, biases, coefficients, or other parameters. Updates may be performed in neural networks using one or more back-propagation algorithms. Iterative and/or recursive updates to weights, biases, coefficients, or other parameters as described above may be performed until currently available training data 404 are exhausted and/or until a convergence test is passed. For the purposes of this disclosure, a "convergence test" is a test for a condition selected to indicate that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

With continued reference to FIG. 4, a computing device, control unit 132, and/or machine learning module 400 may be configured to perform method, method step, sequence of method steps, and/or algorithm described in reference to this figure, in any order and with any degree of repetition. For instance, computing device, control unit 132, and/or machine learning module 400 may be configured to perform a single step, sequence, and/or algorithm repeatedly until a desired or commanded outcome is achieved; repetition of a step or a sequence of steps may be performed iteratively and/or recursively using outputs 408 of previous repetitions as inputs 412 to subsequent repetitions, aggregating inputs 412 and/or outputs 408 of repetitions to produce an aggregate result, reduction or decrement of one or more variables such as global variables, and/or division of a larger processing task into a set of iteratively addressed smaller processing tasks. Computing device, control unit 132, and/or machine learning module 400 may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 4, machine learning process may include at least an unsupervised machine learning process 432. For the purposes of this disclosure, an unsupervised machine learning process is a process that derives inferences in datasets without regard to labels. As a result, an unsupervised machine learning process 432 may be free to discover any structure, relationship, and/or correlation provided in the data. Unsupervised processes 432 may not require a response variable, may be used to find interesting patterns and/or inferences between variables, to determine a degree of correlation between two or more variables, or the like.

With continued reference to FIG. 4, machine learning module 400 may be designed and configured to create machine learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include an elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to a person of ordinary skill in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought. Similar methods to those described above may be applied to minimize error functions, as will be apparent to a person of ordinary skill in the art upon reviewing the entirety of this disclosure.

With continued reference to FIG. 4, machine learning algorithms may include, without limitation, linear discriminant analysis. Machine learning algorithm may include quadratic discriminant analysis. Machine learning algorithms may include kernel ridge regression. Machine learning algorithms may include support vector machines, including without limitation support vector classification-based regression processes. Machine learning algorithms may include stochastic gradient descent algorithms, including classification and regression algorithms based on stochastic gradient descent. Machine learning algorithms may include nearest neighbors algorithms. Machine learning algorithms may include various forms of latent space regularization such as variational regularization. Machine learning algorithms may include Gaussian processes such as Gaussian Process Regression. Machine learning algorithms may include cross-decomposition algorithms, including partial least squares and/or canonical correlation analysis. Machine learning algorithms may include Naive Bayes methods. Machine learning algorithms may include algorithms based on decision trees, such as decision tree classification or regression algorithms. Machine learning algorithms may include ensemble methods such as bagging meta-estimator, forest of randomized trees, AdaBoost, gradient tree boosting, and/or voting classifier methods. Machine learning algorithms may include neural net algorithms, including convolutional neural net processes.

With continued reference to FIG. 4, a machine learning model and/or process may be deployed or instantiated by incorporation into a program, apparatus, system, and/or module. For instance, and without limitation, a machine learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit, to represent a number according to any suitable encoding system including twos complement or the like, or may be stored in any volatile and/or non-volatile memory. Similarly, mathematical operations and input 412 and/or output 408 of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine learning process and/or model, including without limitation any combination of production and/or configuration of non-reconfigurable hardware elements, circuits, and/or modules such as without limitation application-specific integrated circuits (ASICs), production and/or configuration of reconfigurable hardware elements, circuits, and/or modules such as without limitation field programmable gate arrays (FPGAs), production and/or configuration of non-reconfigurable and/or non-rewritable memory elements, circuits, and/or modules such as without limitation non-rewritable read-only memory (ROM), other memory technology described in this disclosure, and/or production and/or configuration of any computing device and/or component thereof as described in this disclosure. Such deployed and/or instantiated machine learning model and/or algorithm may receive inputs 412 from any other process, module, and/or component described in this disclosure, and produce outputs 408 to any other process, module, and/or component described in this disclosure.

With continued reference to FIG. 4, any process of training, retraining, deployment, and/or instantiation of any machine learning model and/or algorithm may be performed and/or repeated after an initial deployment and/or instantiation to correct, refine, and/or improve the machine learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs 408 of machine learning models and/or algorithms, and/or errors and/or error functions thereof, to any thresholds, convergence tests, or the like, and/or may compare outputs 408 of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

With continued reference to FIG. 4, retraining and/or additional training may be performed using any process for training described above, using any currently or previously deployed version of a machine learning model and/or algorithm as a starting point. Training data for retraining may be collected, preconditioned, sorted, classified, sanitized, or otherwise processed according to any process described in this disclosure. Training data 404 may include, without limitation, training examples including inputs 412 and correlated outputs 408 used, received, and/or generated from any version of any system, module, machine learning model or algorithm, apparatus, and/or method described in this disclosure. Such examples may be modified and/or labeled according to user feedback or other processes to indicate desired results, and/or may have actual or measured results from a process being modeled and/or predicted by system, module, machine learning model or algorithm, apparatus, and/or method as "desired" results to be compared to outputs 408 for training processes as described above. Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

With continued reference to FIG. 4, one or more processes or algorithms described above may be performed by at least a dedicated hardware unit 436. For the purposes of this disclosure, a "dedicated hardware unit" is a hardware component, circuit, or the like, aside from a principal control circuit and/or processor performing method steps as described in this disclosure, that is specifically designated or selected to perform one or more specific tasks and/or processes described in reference to this figure, such as without limitation preprocessing and/or sanitization of training data and/or training a machine learning algorithm and/or model. Dedicated hardware unit 436 may include, without limitation, a hardware unit that can perform iterative or massed calculations, such as matrix-based calculations to update or tune parameters, weights, coefficients, and/or biases of machine learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously, in parallel, and/or the like. Such dedicated hardware units 436 may include, without limitation, graphical processing units (GPUs), dedicated signal processing modules, field programmable gate arrays (FPGA), other reconfigurable hardware that has been configured to instantiate parallel processing units for one or more specific tasks, or the like. Computing device, control unit 132, apparatus 100, or machine learning module 400 may be configured to instruct one or more dedicated hardware units 436 to perform one or more operations described herein, such as evaluation of model and/or algorithm outputs, one-time or iterative updates to parameters, coefficients, weights, and/or biases, vector and/or matrix operations, and/or any other operations described in this disclosure.

Figure 5:
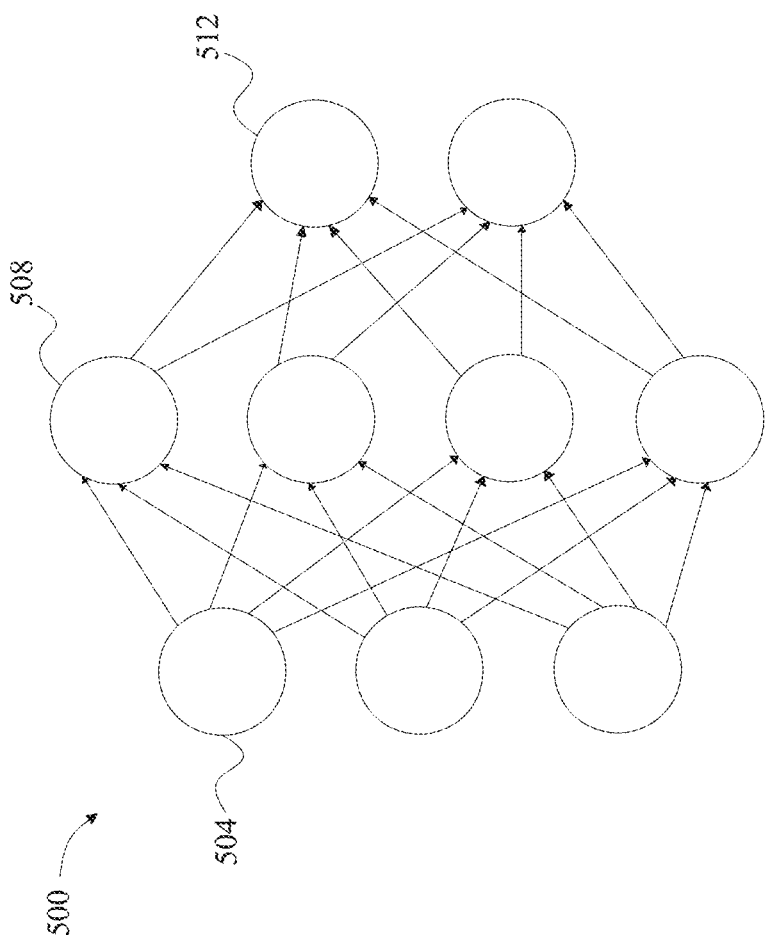
FIG. 5 is a diagram of an exemplary embodiment of a neural network.

Referring now to FIG. 5, an exemplary embodiment of neural network 500 is illustrated. For the purposes of this disclosure, a neural network or artificial neural network is a network of "nodes" or data structures having one or more inputs, one or more outputs, and a function determining outputs based on inputs. Such nodes may be organized in a network, such as without limitation a convolutional neural network, including an input layer of nodes 504, at least an intermediate layer of nodes 508, and an output layer of nodes 512. Connections between nodes may be created via the process of training neural network 500, in which elements from a training dataset are applied to the input nodes, and a suitable training algorithm (such as Levenberg-Marquardt, conjugate gradient, simulated annealing, or other algorithms) is then used to adjust the connections and weights between nodes in adjacent layers of the neural network 500 to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network". As a further nonlimiting example, neural network 500 may include a convolutional neural network comprising an input layer of nodes 504, one or more intermediate layers of nodes 508, and an output layer of nodes 512. For the purposes of this disclosure, a "convolutional neural network" is a type of neural network 500 in which at least one hidden layer is a convolutional layer that convolves inputs to that layer with a subset of inputs known as a "kernel", along with one or more additional layers such as pooling layers, fully connected layers, and the like.

Figure 6:
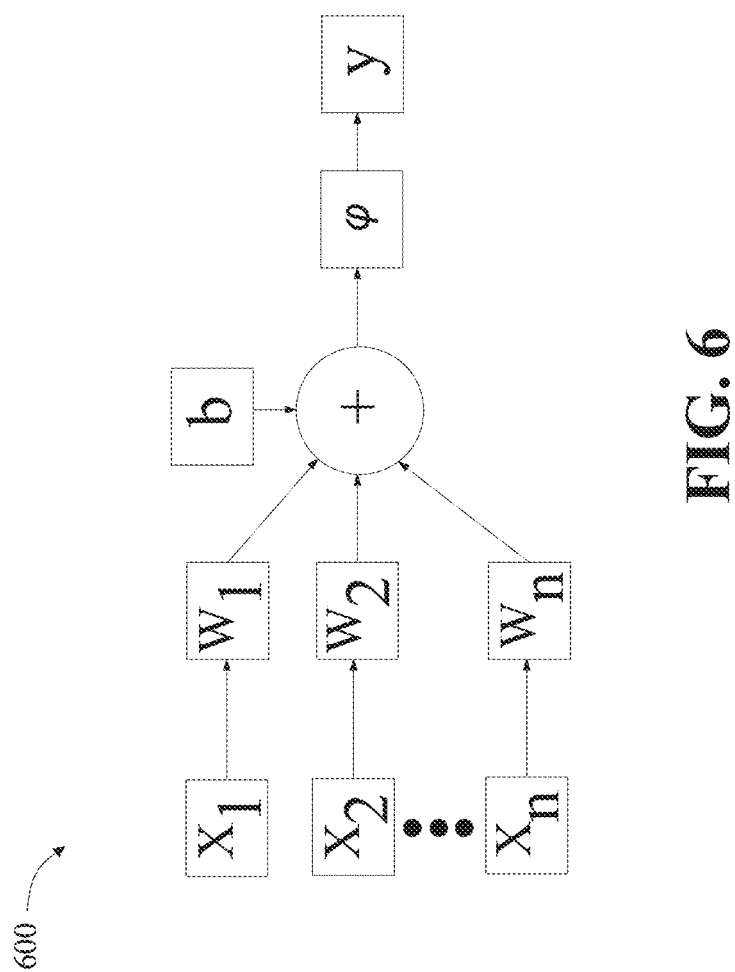
FIG. 6 is a diagram of an exemplary embodiment of a node of a neural network.

Referring now to FIG. 6, an exemplary embodiment of a node 600 of neural network 500 is illustrated. Node 600 may include, without limitation, a plurality of inputs, $x_i$, that may receive numerical values from inputs to neural network 500 containing the node 600 and/or from other nodes 600. Node 600 may perform one or more activation functions to produce its output given one or more inputs, such as without limitation computing a binary step function comparing an input to a threshold value and outputting either a logic 1 or logic 0 output or its equivalent, a linear activation function whereby an output is directly proportional to input, and/or a nonlinear activation function wherein the output is not proportional to the input. Nonlinear activation functions may include, without limitation, a sigmoid function of the form $$f(x) = \frac{1}{1-e^{-x}}$$

given input x, a tan h (hyperbolic tangent) function of the form $$\frac{e^x - e^{-x}}{e^x + e^{-x}},$$

a tan h derivative function such as $f(x) = \tan h^2(x)$, a rectified linear unit function such as $f(x) = \max(0, x)$, a "leaky" and/or "parametric" rectified linear unit function such as $f(x) = \max(ax, x)$ for some value of a, an exponential linear units function such as $$f(x) = \begin{cases} x \text{ for } x \geq 0 \\ \alpha(e^x - 1) \text{ for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x) = x^*\text{sigmoid}(x)$, a Gaussian error linear unit function such as $f(x) = a(1 + \tan h(\sqrt{2/\pi}(x + bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$, that may be used as activation functions. As a nonlimiting and illustrative example, node 600 may perform a weighted sum of inputs using weights, $w_i$, that are multiplied by respective inputs, $x_i$. Additionally or alternatively, a bias b may be added to the weighted sum of the inputs such that an offset is added to each unit in a neural network layer that is independent of the input to the layer. The weighted sum may then be input into a function, φ, which may generate one or more outputs, y. Weight, $w_i$, applied to an input, $x_i$, may indicate whether the input is "excitatory", indicating that it has strong influence on the one or more outputs, y, for instance by the corresponding weight having a large numerical value, or "inhibitory", indicating it has a weak influence on the one more outputs, y, for instance by the corresponding weight having a small numerical value. The values of weights, $w_i$, may be determined by training neural network 500 using training data, which may be performed using any suitable process as described above.

Figure 7:
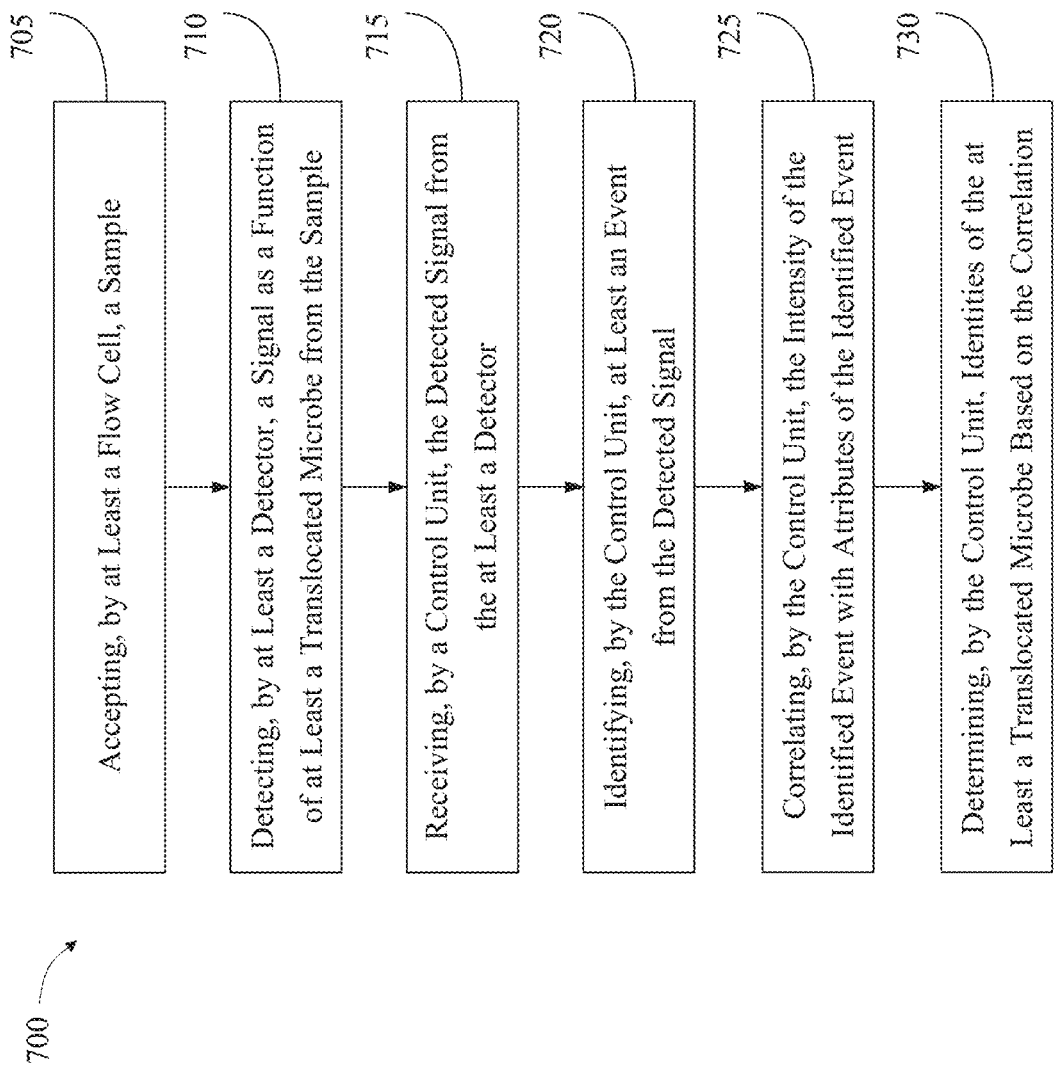
FIG. 7 is a flow diagram of an exemplary embodiment of a method for identification of microbial presence.

Referring now to FIG. 7, an exemplary embodiment of method 700 for identification of microbes 212 is described. At step 705, method 700 includes accepting, by first flow cell 120*a*, a sample comprising at least a microbe 212. This step may be implemented with reference to details described above in this disclosure and without limitation.

With continued reference to FIG. 7, at step 710, method 700 includes detecting, by at least a detector 128, a signal 300*a* as a function of at least a microbe 212, wherein the at least a microbe 212 is translocated from first flow cell 120*a* to second flow cell 120*b* through at least a nanopore 104. This step may be implemented with reference to details described above in this disclosure and without limitation. In one or more embodiments, detected signal 300*a* may include an electrical signal. As a nonlimiting example, detected signal 300*a* may include a resistive pulse.

With continued reference to FIG. 7, at step 715, method 700 includes receiving, by control unit 132, detected signal 300*a* from at least a detector 128. This step may be implemented with reference to details described above in this disclosure and without limitation.

With continued reference to FIG. 7, at step 720, method 700 includes identifying, by control unit 132, at least an event 316 from detected signal 300*a*. This step may be implemented with reference to details described above in this disclosure and without limitation.

With continued reference to FIG. 7, at step 725, method 700 includes correlating, by control unit 132, the intensity of at least an identified event 316 with at least an attribute of the at least an identified event 316. This step may be implemented with reference to details described above in this disclosure and without limitation. In one or more embodiments, correlating the intensity of identified at least an event 316 with at least an attribute of the identified at least an event 316 may involve implementing a machine learning model.

With continued reference to FIG. 7, at step 730, method 700 includes determining, by control unit 132, at least an identity of at least a translocated microbe 212 as a function of the correlation from step 725. This step may be implemented with reference to details described above in this disclosure and without limitation.

Figure 8:
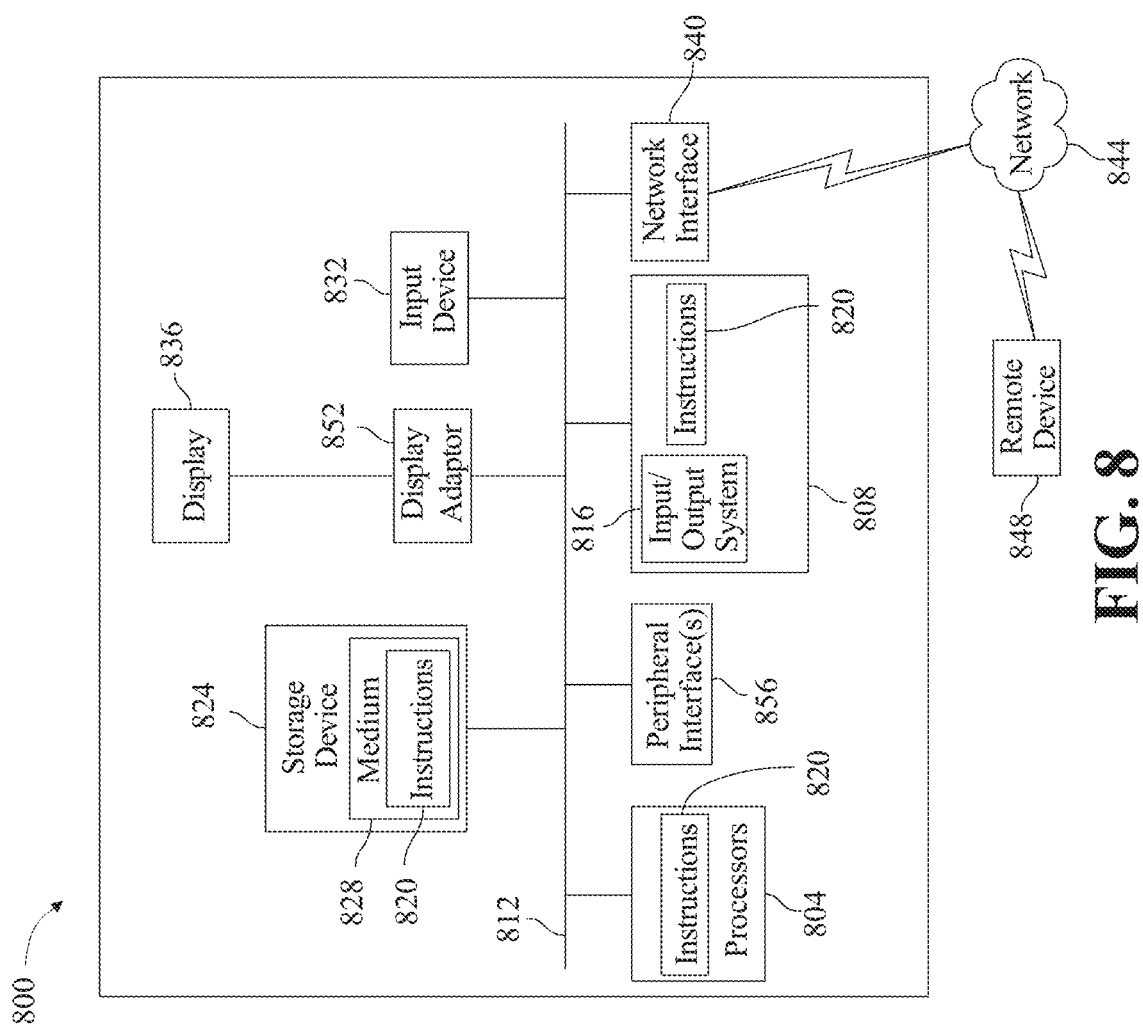
FIG. 8 is a block diagram of an exemplary embodiment of a computing system that can be used to implement any one or more of the methodologies disclosed herein and any one or more portions thereof.

Referring now to FIG. 8, it is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to one of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module. Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission. Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein. Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

With continued reference to FIG. 8, the figure shows a diagrammatic representation of one embodiment of a computing device in the exemplary form of a computing system 800 within which a set of instructions for causing the computing system 800 to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computing system 800 may include a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures. Processor 804 may include any suitable processor, such as without limitation a processor incorporating logical circuitry for performing arithmetic and logical operations, such as an arithmetic and logic unit, which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor, field programmable gate array, complex programmable logic device, graphical processing unit, general-purpose graphical processing unit, tensor processing unit, analog or mixed signal processor, trusted platform module, a floating-point unit, and/or system on a chip.

With continued reference to FIG. 8, memory 808 may include various components (e.g., machine-readable media) including, but not limited to, a random-access memory component, a read only component, and any combinations thereof. In one example, a basic input/output system 816, including basic routines that help to transfer information between elements within computing system 800, such as during start-up, may be stored in memory 808. Memory 808 (e.g., stored on one or more machine-readable media) may also include instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

With continued reference to FIG. 8, computing system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, small computer system interface, advanced technology attachment, serial advanced technology attachment, universal serial bus, IEEE 1394 (FIREWIRE), and any combinations thereof. In one example, storage device 824 (or one or more components thereof) may be removably interfaced with computing system 800 (e.g., via an external port connector (not shown)). Particularly, storage device 824 and an associated machine-readable medium 828 may provide nonvolatile and/or volatile storage of machine-readable instructions, data structures, program modules, and/or other data for computing system 800. In one example, software 820 may reside, completely or partially, within machine-readable medium 828. In another example, software 820 may reside, completely or partially, within processor 804.

With continued reference to FIG. 8, computing system 800 may also include an input device 832. In one example, a user of computing system 800 may enter commands and/or other information into computing system 800 via input device 832. Examples of input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

With continued reference to FIG. 8, user may also input commands and/or other information to computing system 800 via storage device 824 (e.g., a removable disk drive, a flash drive, etc.) and/or network interface device 840. A network interface device, such as network interface device 840, may be utilized for connecting computing system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide-area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computing system 800 via network interface device 840.

With continued reference to FIG. 8, computing system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computing system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for identification of microbial presence, the apparatus comprising:
   a plurality of nanopores;
   at least a nanopore reader, wherein each nanopore reader of the at least a nanopore reader comprises:
      a plurality of flow cells, wherein at least a flow cell within the plurality of flow cells is configured to accept a sample; and
      an electrical detector connected to the plurality of flow cells, the electrical detector configured to detect at least a change in an electrical signal caused by translocation of a microbe and output an electronic communication signal based on the detected at least a change; and
   a control unit communicatively connected to the at least a detector, wherein the control unit comprises:
      digital electronic circuitry configured to receive the electronic communication signal; and
      at least a processor configured by machine executable instructions to:
         identify at least an event from the electronic communication signal;
         correlate an intensity of the at least an identified event with at least an attribute of the at least an identified event; and
         determine at least an identity of the at least a translocated microbe as a function of the correlation.

2. The apparatus of claim 1, wherein the plurality of nanopores is arranged in a line.

3. The apparatus of claim 2, wherein:
   at least a first nanopore within the plurality of nanopores has a first size between 100 nanometers and 20 micrometers;
   at least a second nanopore within the plurality of nanopores has a second size between 100 nanometers and 20 micrometers; and
   the first size is different from the second size.

4. The apparatus of claim 2, wherein:
   each nanopore within the plurality of nanopores has a size between 100 nanometers and 20 micrometers; and
   each nanopore within the plurality of nanopores has a size that is different from the size of a rest of nanopores within the plurality of nanopores.

5. The apparatus of claim 2, wherein:
   at least a first nanopore within the plurality of nanopores has a first geometry;
   at least a second nanopore within the plurality of nanopores has a second geometry; and
   the first geometry is different from the second geometry.

6. The apparatus of claim 2, wherein each nanopore within the plurality of nanopores has a geometry that's different from the geometry of a rest of nanopores within the plurality of nanopores.

7. The apparatus of claim 2, wherein:
at least a first nanopore within the plurality of nanopores has a first voltage difference along a longitudinal axis of the at least a first nanopore;
at least a second nanopore within the plurality of nanopores has a second voltage difference along a longitudinal axis of the at least a second nanopore; and
the first voltage difference is different from the second voltage difference.

8. The apparatus of claim 2, wherein each nanopore within the plurality of nanopores has a voltage difference that's different from the voltage difference of a rest of nanopores within the plurality of nanopores.

9. The apparatus of claim 1, wherein the plurality of nanopores is arranged in a two-dimensional matrix.

10. The apparatus of claim 9, wherein:
the plurality of nanopores is arranged along a first axis, wherein:
at least a first nanopore along the first axis has a first size between 100 nanometers and 20 micrometers;
at least a second nanopore along the first axis has a second size between 100 nanometers and 20 micrometers; and
the first size is different from the second size;
the plurality of nanopores is arranged along a second axis, wherein:
at least a first nanopore along the second axis has a first voltage difference along a longitudinal axis of the at least a first nanopore;
at least a second nanopore along the second axis has a second voltage difference along a longitudinal axis of the at least a second nanopore; and
the first voltage difference is different from the second voltage difference; and
the first axis is different from the second axis.

11. The apparatus of claim 9, wherein:
the plurality of nanopores is arranged along a first axis, wherein:
each nanopore within one or more nanopores along the first axis has a size between 100 nanometers and 20 micrometers; and
each nanopore within one or more nanopores along the first axis has a size that is different from the size of a rest of nanopores within the one or more nanopores along the first axis;
the plurality of nanopores is arranged along a second axis, wherein each nanopore within one or more nanopores along the second axis has a voltage difference that's different from the voltage difference of a rest of nanopores within the one or more nanopores along the second axis; and
the first axis is different from the second axis.

12. The apparatus of claim 9, wherein:
at least a first nanopore within the plurality of nanopores has a first geometry;
at least a second nanopore within the plurality of nanopores has a second geometry; and
the first geometry is different from the second geometry.

13. The apparatus of claim 9, wherein each nanopore within one or more nanopores along a first axis has a geometry that's different from the geometry of a rest of nanopores within the one or more nanopores along the first axis.

14. The apparatus of claim 9, wherein:
a pore surface of at least a first nanopore of the plurality of nanopores is made of a first material;
a pore surface of at least a second nanopore of the plurality of nanopores is made of a second material; and
the first material is different from the second material.

15. The apparatus of claim 1, wherein the plurality of nanopores is arranged in a three-dimensional matrix.

16. The apparatus of claim 15, wherein:
at least a first nanopore within the plurality of nanopores has a first size between 100 nanometers and 20 micrometers;
at least a second nanopore within the plurality of nanopores has a second size between 100 nanometers and 20 micrometers; and
the first size is different from the second size.

17. The apparatus of claim 15, wherein:
each nanopore within the plurality of nanopores has a size between 100 nanometers and 20 micrometers; and
each nanopore within the plurality of nanopores has a size that is different from the size of a rest of nanopores within the plurality of nanopores.

18. The apparatus of claim 15, wherein:
at least a first nanopore within the plurality of nanopores has a first geometry;
at least a second nanopore within the plurality of nanopores has a second geometry; and
the first geometry is different from the second geometry.

19. The apparatus of claim 15, wherein each nanopore within the plurality of nanopores has a geometry that's different from the geometry of a rest of nanopores within the plurality of nanopores.

20. The apparatus of claim 15, wherein:
at least a first nanopore within the plurality of nanopores has a first voltage difference along a longitudinal axis of the at least a first nanopore;
at least a second nanopore within the plurality of nanopores has a second voltage difference along a longitudinal axis of the at least a second nanopore; and
the first voltage difference is different from the second voltage difference.

21. The apparatus of claim 15, wherein each nanopore within the plurality of nanopores has a voltage difference that's different from the voltage difference of a rest of nanopores within the plurality of nanopores.

22. The apparatus of claim 1, wherein:
a first flow cell within the plurality of flow cells is configured to accept a sample;
a second flow cell within the plurality of flow cells is configured to accept a reference;
the first flow cell intersects the second flow cell at a junction; and
at least a nanopore within the plurality of nanopores is located at the junction and connecting between the first flow cell and the second flow cell.

23. The apparatus of claim 1, wherein correlating the intensity of the identified at least an event with the at least an attribute of the identified at least an event comprises:
receiving pattern analysis training data comprising a plurality of training examples as inputs correlated to a plurality of patterns of correlations as outputs;
iteratively training pattern analysis model using the pattern analysis training data; and correlating the intensity of the identified at least an event with the at least an attribute of the identified at least an event using the trained pattern analysis model.

24. The apparatus of claim 1, wherein the detected signal includes an electrical signal.

25. An apparatus for identification of nonviral microbial presence, the apparatus comprising:
at least one nanopore;
a nanopore reader, comprising:
  a plurality of flow cells, wherein at least a flow cell within the plurality of flow cells is configured to accept a sample; and
  an electrical detector connected to the plurality of flow cells, the electrical detector configured to detect at least a change in an electrical signal caused by translocation of a microbe and output an electronic communication signal based on the detected at least a change; and
a control unit communicatively connected to the at least a detector, wherein the control unit comprises:
  digital electronic circuitry configured to receive the electronic communication signal; and
  at least a processor configured by machine executable instructions to:
    identify at least an event from the electronic communication signal;
    correlate an intensity of the identified at least an event with at least an attribute of the identified at least an event; and
    determine at least an identity of the at least a translocated nonviral microbe as a function of the correlation.

26. The apparatus of claim 25, wherein the at least a nanopore has a size between 1 micrometer and 20 micrometers.

27. The apparatus of claim 25, wherein:
a first flow cell within the plurality of flow cells is configured to accept a sample;
a second flow cell within the plurality of flow cells is configured to accept a reference;
the first flow cell intersects the second flow cell at a junction; and
at least a nanopore within the plurality of nanopores is located at the junction and connecting between the first flow cell and the second flow cell.

28. The apparatus of claim 25, wherein correlating the intensity of the detected signal with the at least an attribute of the detected signal comprises:
receiving pattern analysis training data comprising a plurality of training examples as inputs correlated to a plurality of patterns of correlations as outputs;
iteratively training pattern analysis model using the pattern analysis training data; and
correlating the intensity of the identified at least an event with the at least an attribute of the identified at least an event using the trained pattern analysis model.

29. The apparatus of claim 25, wherein the detected signal includes an electrical signal.

30. A method for identification of microbial presence, the method comprising:
accepting, by a first flow cell, a sample comprising at least a microbe;
detecting, by an electrical detector, at least a change in an electrical signal caused by translocation of a microbe, wherein the at least a microbe is translocated from the first flow cell to a second flow cell through at least a nanopore;
outputting an electronic communication signal based on the detected at least a change;
receiving, by a control unit comprising digital electronic circuitry, the electronic communication signal from the electrical detector;
identifying, by the control unit, at least an event from the electronic communication signal;
correlating, by the control unit, an intensity of the identified at least an event with at least an attribute of the identified at least an event; and
determining, by the control unit, at least an identity of the at least a translocated microbe as a function of the correlation.

* * * * *